(12) United States Patent
Evrard et al.

(10) Patent No.: US 7,153,849 B2
(45) Date of Patent: Dec. 26, 2006

(54) ANTIDEPRESSANT ARYLPIPERAZINE DERIVATIVES OF HETROCYCLE-FUSED BENZODIOXANS

(75) Inventors: Deborah Ann Evrard, Hamilton Square, NJ (US); Dahui Zhou, East Brunswick, NJ (US); Gary Paul Stack, Ambler, PA (US); Aranapakam Madumbai Venkatesan, Regopark, NY (US); Amedeo A. Failli, Princeton Junction, NJ (US); Susan Christman Croce, Lambertville, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/659,537

(22) Filed: Sep. 10, 2003

(65) Prior Publication Data
US 2004/0142926 A1     Jul. 22, 2004

Related U.S. Application Data

(60) Provisional application No. 60/410,082, filed on Sep. 12, 2002.

(51) Int. Cl.
A61K 31/55     (2006.01)
A61K 31/497    (2006.01)
C07D 401/06    (2006.01)
C07D 243/06    (2006.01)

(52) U.S. Cl. ............... 514/218; 514/253.03; 540/575; 544/361

(58) Field of Classification Search .......... 544/361; 540/575; 514/218, 253.03
See application file for complete search history.

(56) References Cited

U.S. PATENT DOCUMENTS 5,869,490 A     2/1999  Stack ............... 514/255

FOREIGN PATENT DOCUMENTS

WO     91/13872 A1     9/1991
WO     98/16530 A1     4/1998

OTHER PUBLICATIONS

Robichaud et al. Annual Reports in Medicinal Chemistry, vol. 35, p. 11-20 (2000).*
Artigas, F., et al., "Pindolol induces a rapid improvement of depressed patients treated with serotonin reuptake inhibitors," *Arch Gen Psychiatry*, Mar. 1994, 51, 248-251.
Blier, P., et al., "Effectiveness of pindolol with selected antidepressant drugs in the treatment of major depression," *J. of Clinical Psychopharmacology*, 1995, 15(3), 217-222.
Bundgaard, H., "Means to enhance penetration; Prodrugs as a means to improve the delivery of peptide drugs," *Advanced Drug Deliver Reviews*, 1992, 8, 1-38.

Hall, M.D., et al., "[$^3$H]8-hydroxy-2-(Di-n-propylamino)tetralin binding to pre- and postsynaptic 5-hydroxytryptamine sites in various regions of the rat brain," *J. Neurochem.*, 1985, 44, 1685-1696.
Krogsgaard-Larsen, et al. (Eds.), "Design and Application of Prodrugs," *Texbook of Drug Design and Development*, 1991, Chap. 5, 113-123.
Lazareno, S., et al., "Pharmacological characterization of acetylcholine-stimulated [$^3$S]-GTP$\gamma$S binding mediated by human muscarinic m1-m4 receptors: antagonist studies," *Br. J. Pharmacol.*, 1993, 109, 1120-1127.
Ostrowski, S., "A synthesis of fused pyrimidine mono-n-oxides," *Heterocycles*, 1996, 43(2), p. 389-396.
Perez, V., et al., "Randomised, double-blind, placebo-controlled trial of pindolol in combination with fluoxetine antidepressant treatment," *The Lancet*,m May 31, 1997, 349, 1594-1597.
Tome, M.B., et al., "Serotonergic autoreceptor blocade in the reduction of antidepressant latency: personality variables and response to paroxetine and pindolol," *J. Affect Disord*, 1997, 44, 101-109.
Tome, M.B., et al., "Paroxetine and pindolol: a randomized trial of serotonergic antoreceptor blockade in the reduction of antidepressant latency," *Int. Clin. Psychopharmacol*, 1997, 12, 81-89.
Wilen, S.H., "Tables of Resolving Agents and Optical Resolutions," *Univ. of Notre Dame Press, Notre Dame, IN*, E.L. Eliel (Ed.), 1972, p. 268-298.
Wilen, S.H., et al., "Strategies in optical resolutions," *Tetrahedron*, 1977, 33, 2725-2736.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).

(Continued)

*Primary Examiner*—Johann Richter
*Assistant Examiner*—Ebenezer Sackey
(74) *Attorney, Agent, or Firm*—Woodcock Washburn LLP

(57) ABSTRACT

Compounds of the formula I:

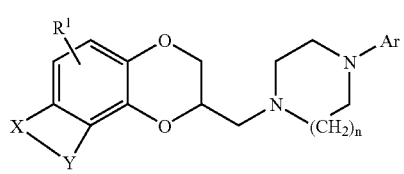

are useful for the treatment of depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive-compulsive disorder, social anxiety disorder, generalized anxiety disorder, obesity, eating disorders such as anorexia nervosa and bulimia nervosa, vasomotor flushing, cocaine and alcohol addiction, sexual dysfunction and related illnesses.

52 Claims, No Drawings

OTHER PUBLICATIONS

Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences,* Apr. 1988, 77(4):285-298.

Eliel, E. L., *Stereochemistry of Carbon Compounds,* McGraw Hill, NY (1962) Ch. 4, pp. 46-87.

Higuchi and Stella (eds.), *Prodrugs as Novel Drug Delivery Systems,* American Chemical Society (1975), pp. 1-115 and 196-223.

Jacques, J. et al., *Enantiomers, Racemates and Resolutions,* Wiley Interscience, NY (1981) pp. 251-434.

*Remington's Pharmaceutical Sciences, 17th* Ed., Gennaro, A. R. (Ed.), Mack Publishing Company, Easton, PA (1985) pp. 1409-1677.

Widder, et al. (ed.), *Methods in Enzymology,* vol. 112, Academic Press (1985), pp. 309-396.

* cited by examiner

ANTIDEPRESSANT ARYLPIPERAZINE DERIVATIVES OF HETROCYCLE-FUSED BENZODIOXANS

CROSS-REFERENCE TO RELATED APPLICATIONS

This application claims the benefit of U.S. application Ser. No. 60/410,082, filed Sep. 12, 2002, the disclosure of which is incorporated herein by reference in its entirety.

FIELD OF THE INVENTION

This invention relates to antidepressant arylpiperazine derivatives of heterocycle-fused benzodioxans, to processes for preparing them, methods of using them and to pharmaceutical compositions containing them.

BACKGROUND OF THE INVENTION

Major depression is a serious health problem affecting more than 5% of the population, with a lifetime prevalence of 15–20%.

Selective serotonin reuptake inhibitors have produced success in treating depression and related illnesses and have become among the most prescribed drugs. They nonetheless have a slow onset of action, often taking several weeks to produce their full therapeutic effect. Furthermore, they are effective in less than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of the Formula I:

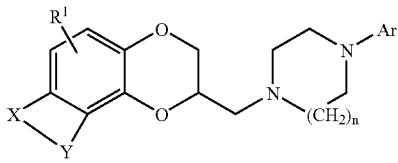

wherein $R^1$ is hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

the group X—Y is —N=C($R^2$)—C($R^3$)=N—, —N=C($R^2$)—C($R^4$)=CH—, —N=C($R^2$)—N=CH—, —N=C($R^2$)—O—, or —NH—C($R^5$)=CH—;

$R^2$ and $R^3$ are, independently, hydrogen, halo, amino, mono- or di-alkylamino in which each alkyl group has 1 to 6 carbon atoms or alkyl of 1 to 6 carbon atoms;

$R^4$ is hydrogen or alkyl of 1 to 6 carbon atoms;

$R^5$ is hydrogen, halo, trifluoromethyl, pentafluoroethyl, or alkyl of 1 to 6 carbon atoms;

Ar is phenyl, naphthyl, indolyl, indazolyl, thienyl, pyridinyl, pyrimidinyl, quinolinyl, benzofuranyl, benzothienyl, benzoisothiazolyl, or benzisoxazolyl, each optionally substituted with one to three substituents independently selected from hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

n is 1 or 2;

or pharmaceutically acceptable salts thereof.

$R^1$ is preferably hydrogen, halo, cyano, trifluoromethyl, alkyl of 1 to 6 carbon atoms or alkoxy of 1 to 6 carbon atoms. More preferably, $R^1$ is hydrogen, halo or alkoxy of 1 to 6 carbon atoms. In still more preferred embodiments of the present invention, $R^1$ is hydrogen.

$R^4$ is preferably hydrogen or alkyl of 1 to 3 carbon atoms.

$R^2$ and $R^3$ are preferably independently selected from hydrogen, amino or alkyl of 1 to 6 carbon atoms. More preferably, $R^2$ and $R^3$ are independently hydrogen or alkyl of 1 to 3 carbon atoms.

$R^5$ is preferably hydrogen, trifluoromethyl, pentafluoroethyl or alkyl of 1 to 6 carbon atoms. More preferably, $R^5$ is hydrogen, trifluoromethyl or alkyl of 1 to 3 carbon atoms.

Ar is preferably phenyl, quinolinyl, benzofuranyl, benzothienyl, or indolyl, each optionally substituted with one to three substituents independently selected from hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

This invention relates to both the R and S stereoisomers of the benzodioxan methylamines as well as to mixtures of the R and S stereoisomers. Throughout this application, the name of the product of this invention, where the absolute configuration of the compounds of the invention is not indicated, is intended to embrace the individual R and S enantiomers as well as mixtures of the two. In some embodiments of the present invention the S enantiomer is preferred.

Where a single stereoisomer is preferred, it may, in some embodiments be provided substantially free of the corresponding enantiomer or diastereomers. Thus, a single stereoisomer substantially free of the corresponding enantiomer or diastereomers refers to a compound which is isolated or separated via separation techniques or prepared free of the corresponding enantiomer or diastereomers. "Substantially free," as used herein, means that the compound is made up of a significantly greater proportion of one stereoisomer. In preferred embodiments, the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures or diastereomeric mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

"Alkyl," as used herein, refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

"Alkanamido," as used herein, refers to the group R—C(=O)—NH— where R is an alkyl group of 1 to 5 carbon atoms.

"Alkanoyloxy," as used herein, refers to the group R—C(=O)—O— where R is an alkyl group of 1 to 5 carbon atoms.

"Alkanesulfonamido," as used herein, refers to the group R—S(O)$_2$—NH— where R is an alkyl group of 1 to 6 carbon atoms.

"Alkoxy," as used herein, refers to the group R—O— where R is an alkyl group of 1 to 6 carbon atoms.

"Carboxamido," as used herein, refers to the group NH$_2$—C(=O)—.

"Carboalkoxy," as used herein refers to the group R—O—C(=O)— where R is an alkyl group of 1 to 5 carbon atoms.

"Halogen" (or "halo"), as used herein, refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I are:
(2S)-2-{[4-(3-chlorophenyl)piperazin-1-yl]methyl}-8-methyl-2,3-dihydro[1,4]dioxino[2,3-f]quinoline;
(2S)-2-{[4-(4-chlorophenyl)piperazin-1-yl]methyl}-8-methyl-2,3-dihydro[1,4]dioxino[2,3-f]quinoline;
(2S)-2-{[4-(3,4-dichlorophenyl)piperazin-1-yl]methyl}-8-methyl-2,3-dihydro[1,4]dioxine[2,3-f]quinoline;
(2S)-2-{[4-(2-methoxyphenyl)piperazin-1-yl]methyl}-8-methyl-2,3-dihydro[1,4]dioxino[2,3-f]quinoline;
(2S)-2-{[4-(3-methoxyphenyl)piperazin-1-yl]methyl}-8-methyl-2,3-dihydro[1,4]dioxino[2,3-f]quinoline;
(2S)-2-{[4-(4-methoxyphenyl)piperazin-1-yl]methyl}-8-methyl-2,3-dihydro[1,4]dioxino[2,3-f]quinoline;
(2S)-2-{[4-(dihydrobenzo[1,4]dioxin-5-yl)piperazin-1-yl]methyl}-8-methyl-2,3-dihydro[1,4]dioxino[2,3-f]quinoline;
(2S)-8-methyl-2-[4-(3-trifluoromethyl-phenyl)piperazin-1-ylmethyl]-2,3-dihydro[1,4]dioxine[2,3-f]quinoline;
(2S)-8-methyl-2-[4-(3-fluorophenyl)piperazin-1-ylmethyl]-2,3-dihydro[1,4]dioxine[2,3-f]quinoline;
(2S)-2-{[4-(2,3-dimethylphenyl)piperazin-1-yl]methyl}-8-methyl-2,3-dihydro[1,4]dioxino[2,3-f]quinoline;
(2S)-2-{[4-(3,4-dimethylphenyl)piperazin-1-yl]methyl}-8-methyl-2,3-dihydro[1,4]dioxino[2,3-f]quinoline;
(2S)-8-methyl-2-[(4-quinolin-2-yl)piperazin-1-yl)methyl]-2,3-dihydro[1,4]dioxino[2,3-f]quinoline;
(2S)-8-methyl-2-{4-(6-nitroquinolin-2-yl)piperazin-1-yl]methyl)-2,3-dihydro[1,4]dioxino[2,3-f]quinoline;
(2S)-8-methyl-2-{4-(6-chloroquinolin-2-yl)piperazin-1-yl]methyl)-2,3-dihydro[1,4]dioxino[2,3-f]quinoline;
2-(4-{[(2S)-8-methyl-2,3-dihydro[1,4]dioxino[2,3-f]quinolin-2-yl]methyl}piperazin-1-yl}quinoline-6-carbonitrile;
(2S)-2-{[4-(1-benzofuran-3-yl)-1-piperazinyl]methyl}-8-methyl-2,3-dihydro[1,4]dioxino[2,3-f]quinoline;
(2S)-2-{[4-(5-fluoro-1-benzofuran-3-yl)-1-piperazinyl]methyl}-8-methyl-2,3-dihydro[1,4]dioxino[2,3-f]quinoline;
(2S)-2-{[4-(7-methoxy-1-benzofuran-3-yl)-1-piperazinyl]methyl}-8-methyl-2,3-dihydro[1,4]dioxino[2,3-f]quinoline;
(2S)-8-methyl-2-{[(2S)-2-methyl-4-quinolin-2-ylpiperazin-1-yl]methyl}-2,3-dihydro[1,4]dioxino[2,3-f]quinoline;
2-((3R)-3-methyl-4-{[(2S))-8-methyl-2,3-dihydro[1,4]dioxino[2,3-f]quinolin-2-yl]methyl}piperazin-1-yl]quinoline-6-carbonitrile;
(2S)-8-methyl-2-{[(2R)-2-methyl-4-quinolin-2-ylpiperazin-1-yl]methyl}-2,3-dihydro[1,4]dioxino[2,3-f]quinoline;
(2S)-8-methyl-2-{[4-(2-naphthyl)piperazin-1-yl]methyl}-2,3-dihydro[1,4]dioxino[2,3-f]quinoline;
(2S)-2-[4-8-methyl-2,3-dihydro-[1,4]dioxino[2,3-f]quinolin-2-yl)-piperazin-1-yl]-quinoline-6-carboxylic acid amide;
(2S)-2-[4-(2,3-Dihydro-[1,4]dioxino[2,3-f]quinolin-2-ylmethyl)-piperazin-1-yl]-quinoline-6-carbonitrile;
(2S)-2-[4-(8-Ethyl-2,3-dihydro-[1,4]dioxino[2,3-f]quinolin-2-ylmethyl)-piperazin-1-yl]-quinoline-6-carbonitrile;
(2S)-2-[4-(2-Methyl-7,8-dihydro-1,6,9-trioxa-3-aza-cyclopenta[a]naphthalen-8-ylmethyl)-piperazin-1-yl]-quinoline-6-carbonitrile;
(2S)-2-{[4-(6-Bromoquinolin-2-yl)piperazin-1-yl]methyl}-8-methyl-2,3-dihydro[1,4]dioxino[2,3-f]quinoline;
(2S)-2-{[4-(6-Bromoquinolin-2-yl)piperazin-1-yl]methyl}-8-methyl-2,3-dihydro[1,4]dioxino[2,3-f]quinoline;
(2S)-2-{[4-(6-methoxyquinolin-2-yl)piperazin-1-yl]methyl]-8-methyl-2,3-dihydro[1,4]dioxino[2,3-f]quinoline;
(2S)-2-{[4-(6-Trifluoromethoxyquinolin-2-yl)piperazin-1-yl]methyl}-8-methyl-2,3-dihydro[1,4]dioxino[2,3-f]quinoline;
2-[4-(6-Fluoro-quinolin-2-yl)-piperazin-1-ylmethyl]-8-methyl-2,3-dihydro-[1,4]dioxino[2,3-f]quinoline;
(2S)-2-{[4-(6-methoxyquinolin-2-yl)-1,4-diazepan-1-yl]methyl]-8-methyl-2,3-dihydro[1,4]dioxino[2,3-f]quinoline;

2-(4-{[(2S)-8-Methyl-2,3-dihydro[1,4]dioxino[2,3-f]quinolin-2-yl]methyl}-1,4-diazepan-1-yl)quinoline-6-carbonitrile;

(2S)-2-{[4-(6-Trifluoromethoxy-quinolin-2-yl)-1,4-diazepan-1-yl]methyl]-8-methyl-2,3-dihydro[1,4]dioxino[2,3-f]quinoline;

2-[4-(6-Fluoro-quinolin-2-yl)-[1,4]diazepan-1-ylmethyl]-8-methyl-2,3-dihydro-[1,4]dioxino[2,3-f]quinoline;

(2S)-2-{[4-(6-Bromo-quinolin-2-yl)-1,4-diazepan-1-yl]methyl]-8-methyl-2,3-dihydro[1,4]dioxino[2,3-f]quinoline;

8-Methyl-2-(4-quinolin-2-yl-[1,4]diazepan-1-ylmethyl)-2,3-dihydro-[1,4]dioxino[2,3-f]quinoline; and 8-Methyl-2-[4-(4-methyl-quinolin-2-yl)-[1,4]di azepan-1-ylmethyl]-2,3-dihydro[1,4]dioxino[2,3-f]quinoline;

and pharmaceutically acceptable salts thereof.

Compounds of the present invention are prepared in accordance with the following general description and specific examples. Variables used are as defined for Formula I, unless otherwise noted. Specifically (Scheme 1), the appropriately substituted arylpiperazine is combined with a suitably substituted benzodioxanmethyl sulfonate (e.g., R is 4-methylphenyl or 4-bromopheneyl) or halide in a solvent such as dimethyl sulfoxide and heated to a temperature of 50–100° C. for several hours as illustrated below.

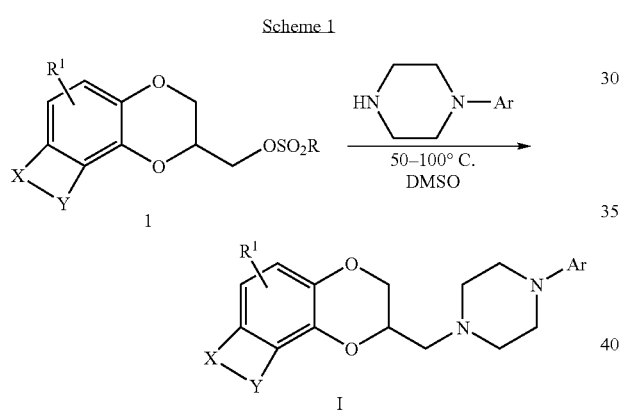

The arylpiperazines appropriate to the chemistry of Scheme 1 are known in the literature or may be prepared by those skilled in the art.

The 2,3-dihydro-1,4-dioxino[2,3-f]quinolin-2-ylmethyl-tosylates in which $R^2$ is hydrogen (R is 4-methylphenyl) appropriate to the chemistry in Scheme 1 can be prepared as illustrated in Scheme 2 below. Specifically, the appropriately substituted nitroguaiacol (2) is alkylated with allyl bromide in the presence of a suitable base such as sodium hydride to produce (3) and then demethylated by a reagent such as sodium hydroxide. The resulting 4-nitro-2-allyloxyphenol (4) is then alkylated with glycidyl tosylate or an epihalohydrin in the presence of a base such as sodium hydride to produce (5) and heated in a high boiling solvent such as mesitylene or xylene to effect both rearrangement of the allyl group and cyclization to the dioxan ring. The resulting primary alcohol (6) is converted to the tosylate by reaction with p-toluenesulfonyl chloride in the presence of a tertiary amine or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene to produce (7). Allylic oxidation with selenium dioxide in refluxing dioxane/water gives the o-nitrocinnamaldehyde, which upon reduction with iron in acetic acid cyclizes to the 2,3-dihydro-1,4-dioxino[2,3-f]quinoline-2-methyl-tosylate (8).

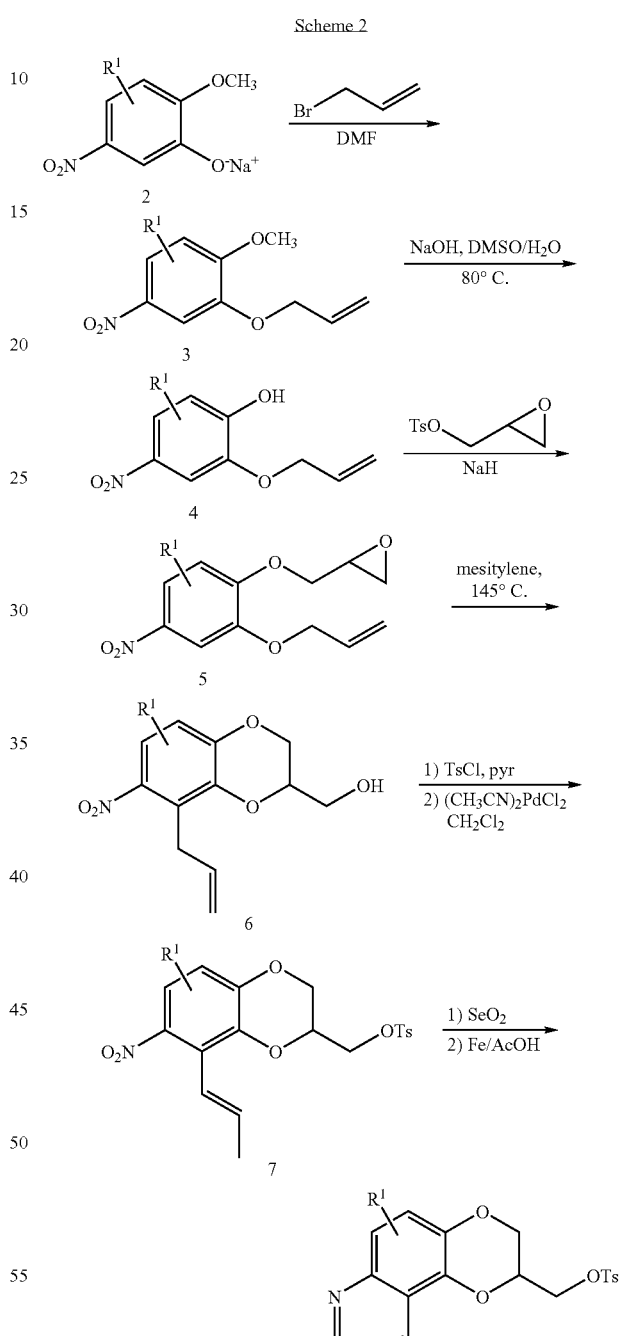

The 2,3-dihydro-1,4-dioxino[2,3-f]quinolin-2-ylmethyl-tosylates in which $R^2$ is alkyl may be prepared from the nitro olefin described above in the manner described in Scheme 3. The rearranged olefin (7) is treated sequentially with ozone and a tertiary amine or with osmium tetroxide and sodium periodate to give the o-nitrobenzaldehyde (9). Condensation with the appropriate triphenyl phosphoranylidene ketone under Wittig conditions gives the o-nitrostyryl ketone (10), which upon reduction by iron in acetic acid, cyclizes to the corresponding 2,3-dihydro-1,4-dioxino[2,3-f]-quinoline-2-methyltosylate (11). Replacement of the tosylate with the appropriately substituted arylpiperazine as above gives the title compounds of the invention.

above to produce (13) and rearranged in refluxing mesitylene. Cyclization to the benzodioxan methanol is effected by treatment with sodium bicarbonate in ethanol and the alcohol (14) is converted to the tosylate. After rearrangement of the double bond by treatment with catalytic bis-acetonitrile palladium chloride in refluxing methylene chloride to produce 15 and cleavage with ozone or osmium tetroxide/sodium periodate as described above, the resulting aldehyde (16) is regioselectively nitrated with a combination of nitric acid and tin (IV) chloride to produce (9).

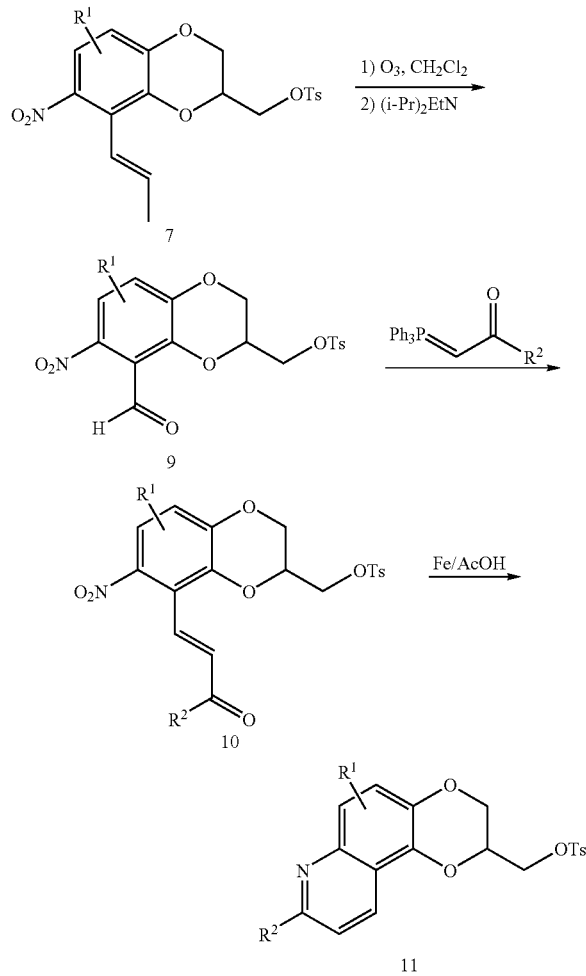

Scheme 3

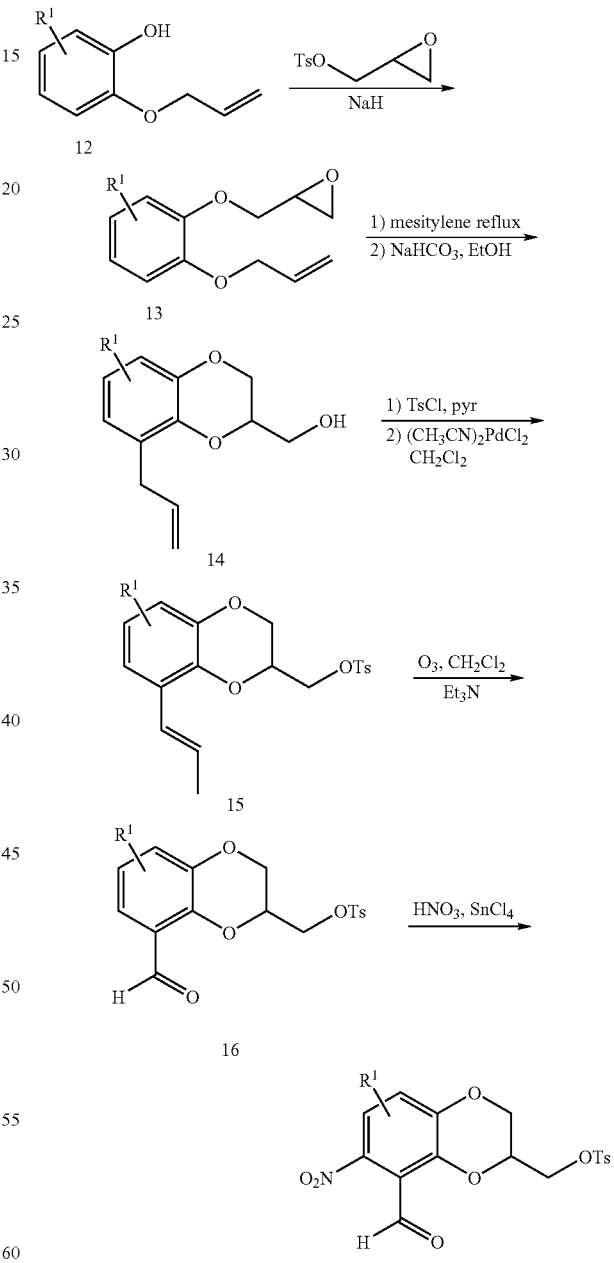

Scheme 4

Substitution of trimethyl phosphonoacetate for the triphenylphosphoranylidene ketone in the Wittig procedure above, followed by reduction of the nitro group with tin (II) chloride and cyclization in acid gives the compounds of the invention in which $R^2$ is hydroxy. Alkylation of this hydroxy derivative by a suitable alkyl halide or tosylate in the presence of base gives the compounds of the invention in which $R^2$ is alkoxy. Treatment of the hydroxy derivative with an inorganic acid chloride such as phosphoryl chloride or bromide gives the compounds of the invention in which $R^2$ is halo. Substitution of diethyl cyanomethylphosphonate for the triphenyl-phosphoranylidene ketone in the Wittig procedure above, followed by reduction of the nitro group with tin (II) chloride and cyclization in acid gives the compounds of the invention in which $R^2$ is amino.

The o-nitrobenzaldehyde (9) used in the Wittig chemistry described in Scheme 3 may be alternatively prepared as shown in Scheme 4. The appropriate mono-allylated catechol (12) is elaborated with glycidyl tosylate as described Compounds of the invention in which $R^1$ is attached to position 6 of the 2,3-dihydro-1,4-dioxino[2,3-f]quinoline may be alternatively prepared by a variation of the Skraup quinoline synthesis according to Scheme 5. The appropriately substituted benzodioxan methyltosylate (17) is nitrated under standard conditions with nitric acid in a solvent such as dichloroethane and the resulting nitro compound (18) reduced by treatment with hydrogen in the presence of a catalyst such as platinum on sulfide carbon. Treatment of the resulting aniline (19) with acrolein in the presence of hydrogen chloride and an oxidant such as p-chloranil or naphthoquinone gives the corresponding 2,3-dihydro-1,4-dioxino[2,3-f]quinoline (20). Replacement of the tosylate with the appropriately substituted arylpiperazine as above gives the title compounds of the invention.

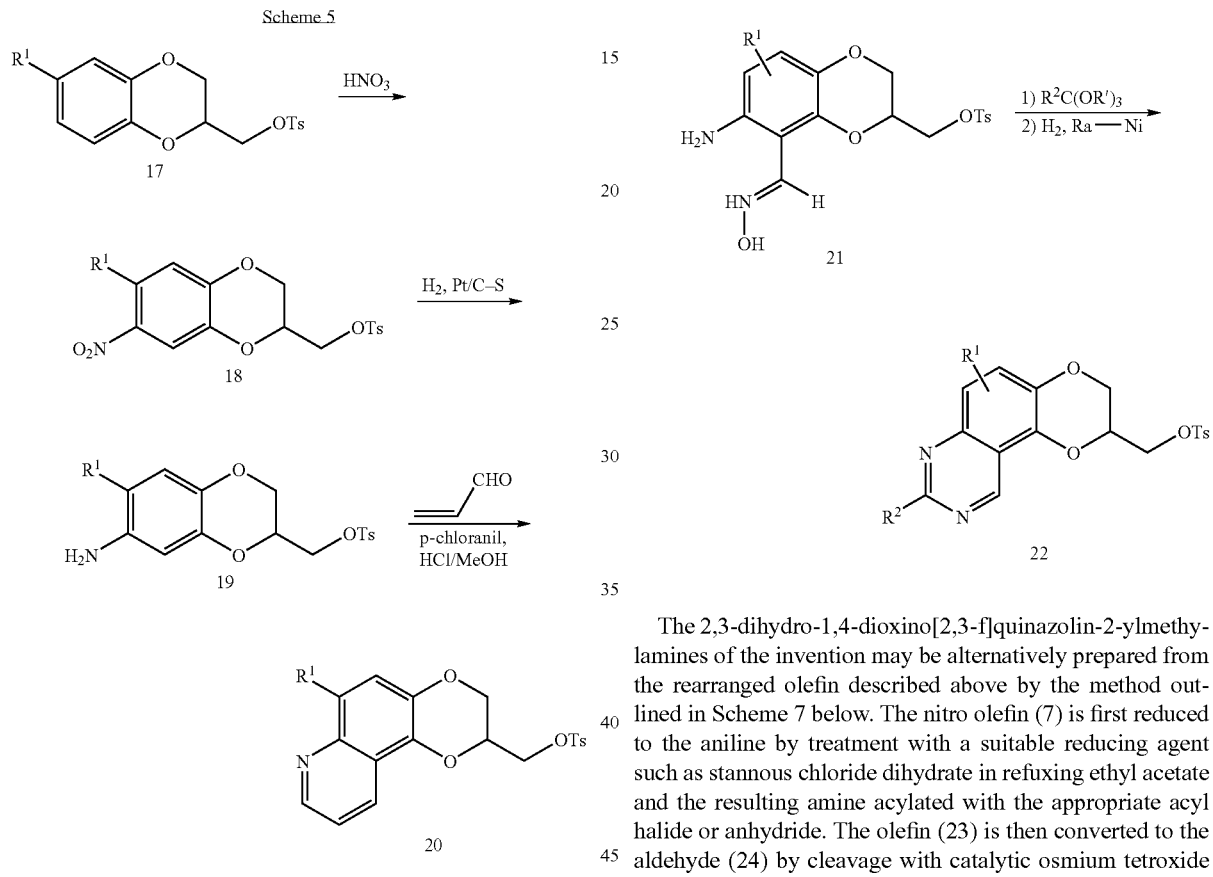

The 2,3-dihydro-1,4-dioxino[2,3-f]quinazolin-2-ylmethylamines of the invention are prepared as illustrated below (Scheme 6). The o-nitrobenzaldehyde (9) described above is converted to the oxime (21) by treatment with hydroxylamine hydrochloride in the presence of a suitable base such as sodium acetate and the nitro group reduced to the amine by hydrogenation over palladium on carbon. Cyclization to the quinazoline N-oxide is effected by treatment at reflux with the appropriate ortho ester according to the method of Ostrowski (*Heterocycles*, vol. 43, No. 2, p. 389, 1996). The quinazoline N-oxide may be reduced to the quinazoline (22) by a suitable reducing agent such as hydrogen over Raney-nickel. Alternatively, an extended period of reflux in the ortho ester gives the reduced quinazoline directly via a disproportionation reaction and the 2,3-dihydro-1,4-dioxino[2,3-f]quinazoline-2-methyltosylate may be isolated by column chromatography. Replacement of the tosylate or halide with the appropriately substituted arylpiperazine in some high boiling solvent such as dimethyl sulfoxide gives the title compounds of the invention.

The 2,3-dihydro-1,4-dioxino[2,3-f]quinazolin-2-ylmethylamines of the invention may be alternatively prepared from the rearranged olefin described above by the method outlined in Scheme 7 below. The nitro olefin (7) is first reduced to the aniline by treatment with a suitable reducing agent such as stannous chloride dihydrate in refuxing ethyl acetate and the resulting amine acylated with the appropriate acyl halide or anhydride. The olefin (23) is then converted to the aldehyde (24) by cleavage with catalytic osmium tetroxide in the presence of excess sodium periodate. Cyclization directly to the 2,3-dihydro-1,4-dioxino[2,3-f]quinazoline-2-methyltosylate (22) or halide is effected by treatment of the amido aldehyde (24) with ammonia and replacement of the tosylate or halide with the appropriately substituted piperazine in some high boiling solvent such as dimethyl sulfoxide as described above gives the title compounds of the invention.

-continued

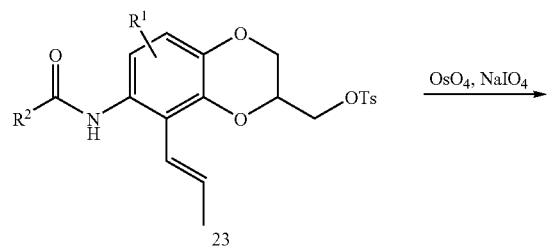

23

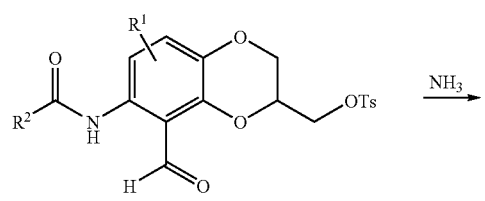

24

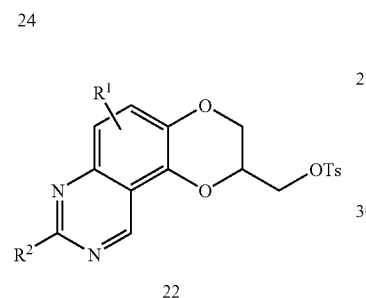

22

-continued

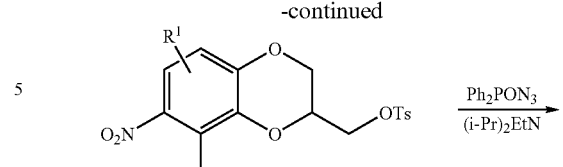

25

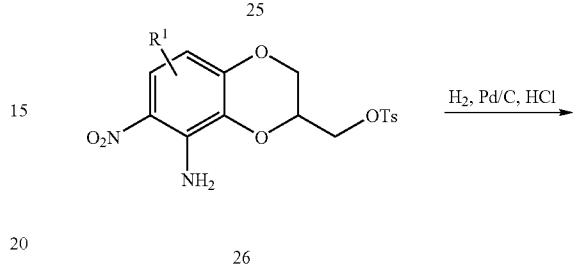

26

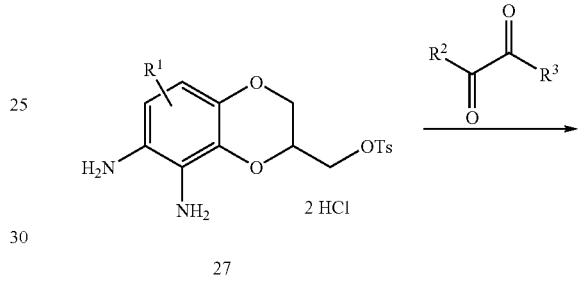

27

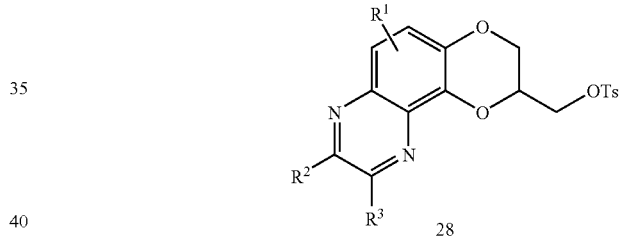

28

The 2,3-dihydro-1,4-dioxino[2,3-f]quinoxalin-2-ylm-ethylamines of the invention are prepared as illustrated in Scheme 8 below. The o-nitrobenzaldehyde (9) described above is oxidized to the o-nitrobenzoic acid (25) by a suitable oxidant such as chromium trioxide (Jones' oxidation) or sodium chlorite and the acid converted to the o-nitroaniline (26) with diphenylphosphoryl azide (DPPA) in the presence of a tertiary base such as diisopropylethylamine. Reduction of the resulting nitroaniline to the diamine (27) with hydrogen and palladium on carbon and cyclization by treatment with the appropriate dicarbonyl compound (for example, glyoxal, 2,3-butanedione, 3,4-hexanedione) gives the 2,3-dihydro-1,4-dioxino[2,3-f]quinoxaline-2-methyltosylate (28). Replacement of the tosylate with the appropriately substituted arylpiperazine in some high boiling solvent such as dimethyl sulfoxide gives the title compounds of the invention.

The 7,8-dihydro[1,4]dioxino[2,3-g][1,3]benzoxazol-8-yl-methylamines of the invention are prepared as illustrated in Scheme 9 below. The o-amidobenzaldehyde (24) described in Scheme 7 is converted to the phenol (29) by treatment with meta-chloroperoxybenzoic acid in a Baeyer-Villager reaction and cyclization to the 7,8-dihydro[1,4]dioxino[2,3-g][1,3]benzoxazole (30) is effected by treatment at reflux with an appropriate dehydrating agent such as an ortho ester or an acid catalyst such as o-toluenesulfonic acid. Replacement of the tosylate with the appropriately substituted arylpiperazine in some high boiling solvent such as dimethyl sulfoxide gives the title compounds of the invention.

Scheme 8

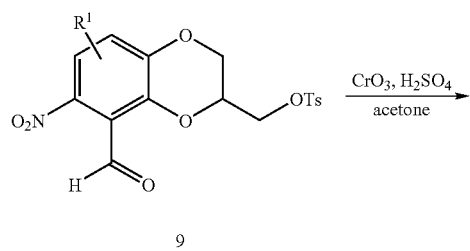

9

Scheme 9

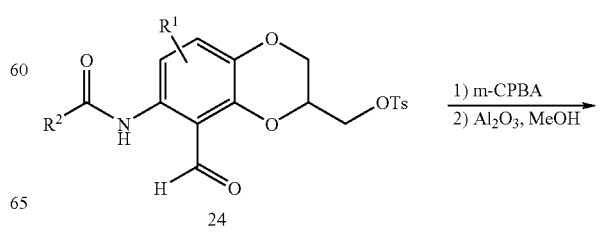

24

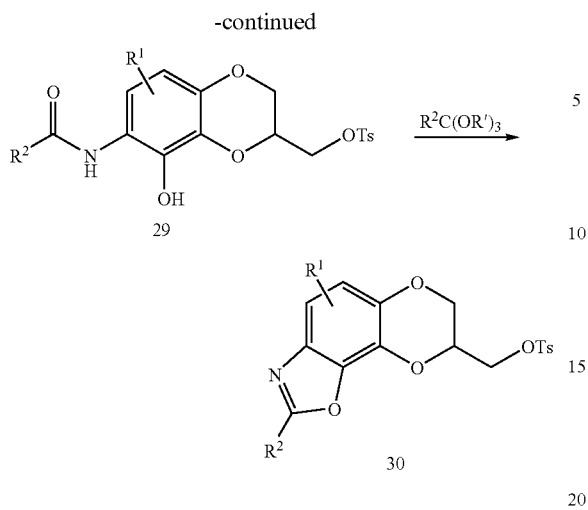

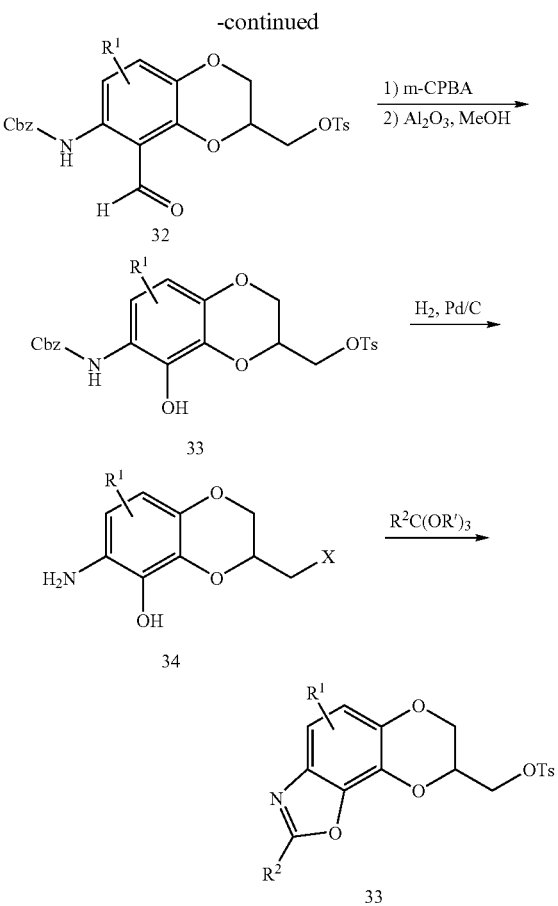

Alternatively (Scheme 10), the nitro olefin (7) may be reduced with tin (II) chloride as described in Scheme 7 above and protected with a suitable protecting group such as carbobenzoxy (Cbz) before the olefin is cleaved to the aldehyde (32) by treatment with osmium tetroxide/sodium periodate and the aldehyde converted to a phenol (33) by the Baeyer-Villager procedure. Deprotection by treatment with hydrogen over palladium on carbon gives the o-aminophenol, (34) which is cyclized to the 7,8-dihydro[1,4]dioxino[2,3-g][1,3]benzoxazole (30) by treatment with the appropriate ortho ester, carboxylic acid or anhydride. Treatment of the o-aminophenol with cyanogen bromide or chloride or a suitably substituted carbamoyl chloride leads to compounds of the invention in which $R^2$ is amino. Treatment of the o-aminophenol with carbonyl diimidazole gives the oxazolone that leads to compounds of the invention in which $R^2$ is halo via treatment with an inorganic anhydride such as phosphoryl chloride or bromide. Replacement of the tosylate with the appropriately substituted arylpiperazine as above gives the title compounds of the invention.

Scheme 10

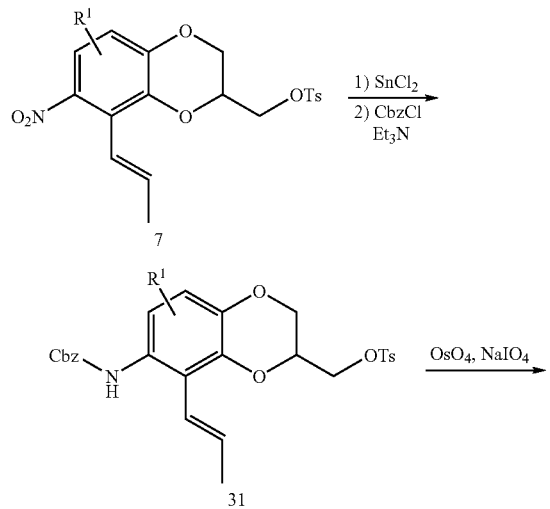

Compounds of the invention in which $R^1$ is hydrogen and $R^2$ is alkyl are most conveniently prepared according to Scheme 11 below. The appropriate 2',3',4'-trihydroxyacylphenone (35) is regioselectively alkylated with glycidyl tosylate or an epihalohydrin in the presence of a base such as sodium carbonate to give the corresponding 7-acyl-8-hydroxybenzodioxan-2-methanol (36). Following conversion of the ketone to the oxime (37) by reaction with hydroxylamine hydrochloride and sodium acetate, cyclization to the oxazole (38) is effected by treatment with phosphoryl chloride in the appropriate dimethylalkanoic acid amide. The resulting 7,8-dihydro-1,6,9-trioxa-3-azacyclopenta[a]naphthalene-8-methanol is converted to the tosylate (39) by treatment with p-toluenesulfonyl chloride in pyridine and combined with the appropriate arylpiperazine as described above to give the title compounds of the invention.

Scheme 11

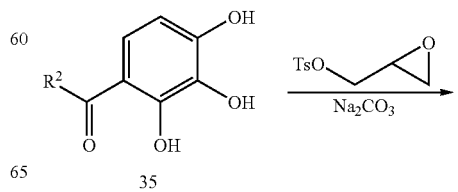

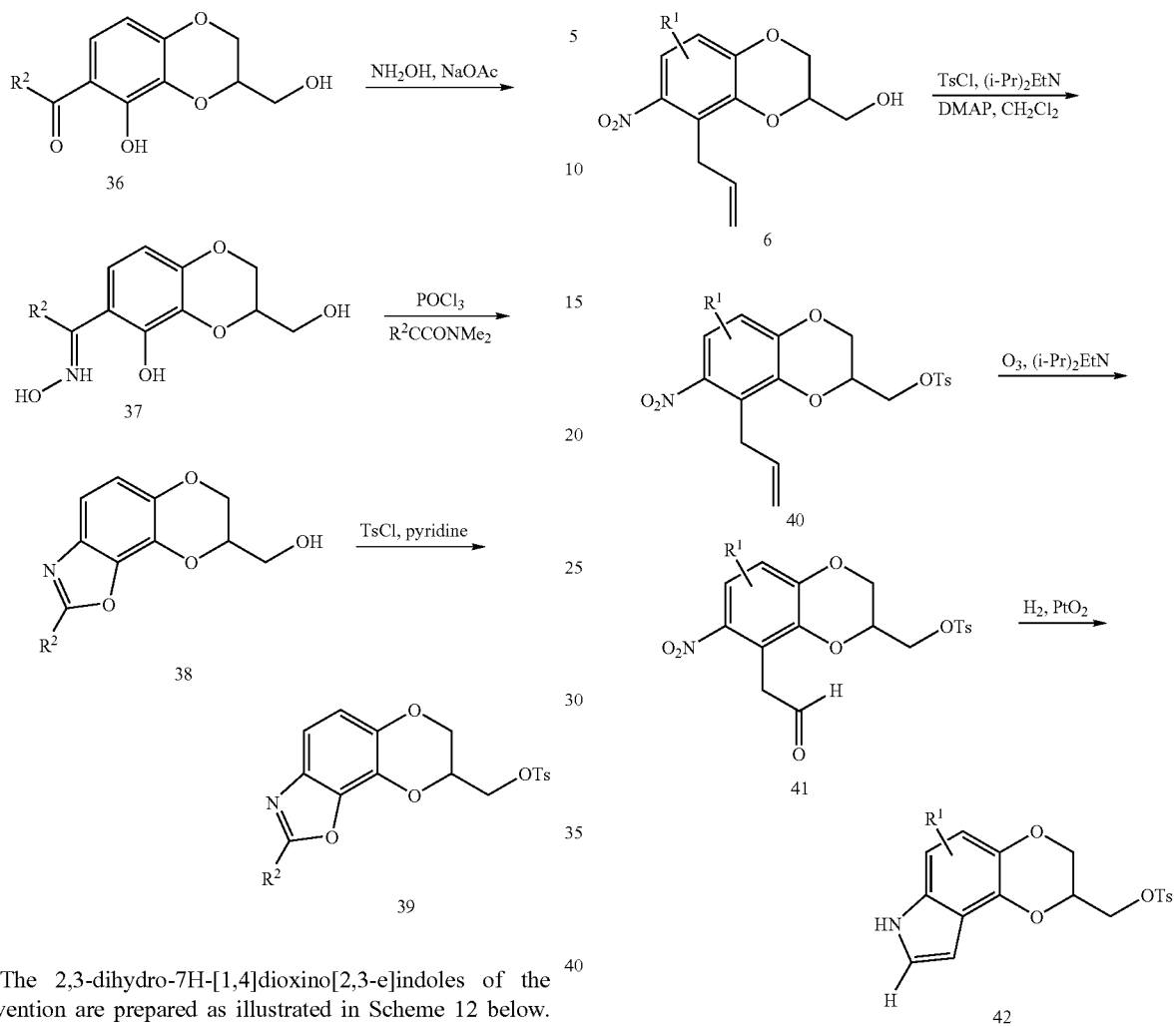

The 2,3-dihydro-7H-[1,4]dioxino[2,3-e]indoles of the invention are prepared as illustrated in Scheme 12 below. Specifically, the primary alcohol (6) from the Claisen rearrangement described in Scheme 2 is converted to the tosylate (40) by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then cleaved to the aldehyde (41) by treatment with ozone at low temperature, followed by workup with a tertiary base such as diisopropylethylamine or triethylamine, or by treatment with catalytic osmium tetroxide and sodium periodate. Reduction of the nitro group with hydrogen over platinum oxide leads directly to formation of the indole (42) in which $R^5$ is hydrogen. Alternatively, the aldehyde may be treated with an appropriate alkyl Grignard reagent or with trifluoromethyl trimethylsilane in the presence of cesium fluoride, then oxidized to a ketone with a suitable oxidant such as pyridinium chlorochromate (PCC) or the Swern reagent and reduced with hydrogen over platinum oxide to give the indoles in which $R^5$ is alkyl or trifluoromethyl. Replacement of the tosylate with the appropriately substituted arylpiperazine in some high boiling solvent such as dimethyl sulfoxide gives the title compounds of the invention.

The 2,3-dihydro-7H-[1,4]dioxino[2,3-e]indoles of the invention may alternatively be prepared following procedure (Scheme 13). The o-nitrobenzaldehyde (9) is condensed with the appropriate nitroalkane in the presence of a suitable base catalyst to yield the corresponding o,β-dinitrostyrene (43). Reduction of both nitro groups with hydrogen over palladium on carbon is accompanied by cyclization to form the indole (44). Replacement of the tosylate with the appropriately substituted arylpiperazine as above gives the title compounds of the invention.

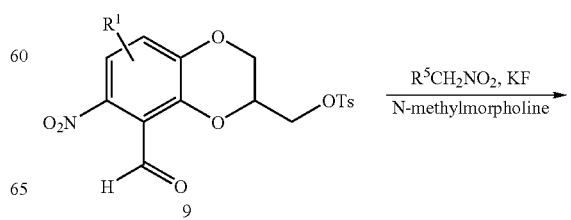

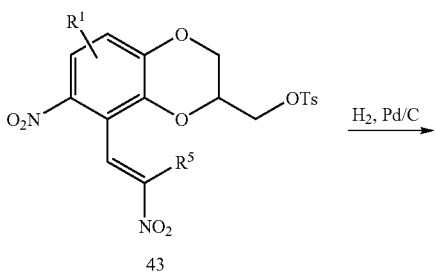

In yet another method, compounds of the present invention may be prepared in accordance with Scheme 14. The synthesis of compound I is comprised of steps that begin with halogenation of 45 where R' is alkyl of 1–6 carbon atoms, with reagents such as N-halosuccinimide in acetonitrile to give 46 (where Hal is halogen such as Br, Cl or I). Deprotection of 46 with Lewis acids such as boron tribromide, boron trichloride, aluminum trichloride, ferric chloride, or trimethylsilyl iodide in a suitable solvent such as methylene chloride, or with strong protic acids such as HBr and HCl gives the salt 47. Free base 47 may be obtained by neutralization with an Amberlyst A-21 resin slurry in polar solvents such as ethanol or methanol. Alkylation of 47, either as the free base or as the salt, with benzyl or substituted benzyl protected glycidyl ethers

where R'' is benzyl, substituted benzyl such as 4-bromobenzyl, 3,4-dimethoxybenzyl, 2- or 4-nitrobenzyl, or 4-methoxybenzyl) in suitable polar solvents such as dimethyl sulfoxide, dimethyl formamide, or dimethyl acetamide in the presence of bases such as sodium carbonate, potassium carbonate, or triethylamine gives 48. The compound 48 is then cyclized using palladium catalysts such as tris(dibenzylideneacetone)dipalladium, tetrakis(triphenylphosphine) palladium, or palladium acetate with ligands from the group consisting of (±) BINAP and separate enantiomers thereof, (±) Tol-BINAP and separate enantiomers thereof; 1-1'-bis (diphenylphosphino) ferrocene, 1,3-bis(diphenylphosphino) propane, and 1,2 bis(diphenyl-phosphino)ethane in the presence of bases such as NaH, LiH, KH, potassium carbonate, sodium carbonate, titanium carbonate, cesium carbonate, potassium t-butoxide or potassium phosphate tribasic in a suitable solvent such as toluene or, alternatively, with copper catalyst such as copper iodide in the presence of bases such NaH, LiH, KH in a suitable solvent such as toluene to afford 49. Deprotection of 49 with Lewis acids such as boron tribromide, boron trichloride, aluminum trichloride, ferric chloride, trimethylsilyl iodide in a suitable solvent such as methylene chloride, or with strong protic acids such as HBr and HCl or under reductive cleavage conditions using Pd catalyst and hydrogen transfer reagents such as hydrogen, cyclohexene, methyl cyclohexene, or ammonium formate gives 50. The hydroxyl moiety of 50 can be activated with an aryl- or alkyl-sulfonyl chloride such as p-toluenesulfonyl chloride, methanesulfonyl chloride, 2-, 3- or 4-nitrobenzenesulfonyl chloride, or 2- or 4-bromobenzenesulfonyl chloride in the presence of bases such as triethylamine or pyridine in suitable solvents such as methylene chloride, THF, or toluene to afford 51 where R''' is sulfonate such as p-toluenesulfonate, methanesulfonate, 2-, 3-, or 4-nitrobenzenesulfonate, or 2- or 4-bromobenzenesulfonate. The final coupling of 51 with arylpiperazines appropriate to the invention, in the presence of bases such as diisopropyl ethylamine, potassium carbonate, or sodium carbonate in polar solvents such as THF, dioxane, DMSO, DMF, or DMA affords compounds of Formula I.

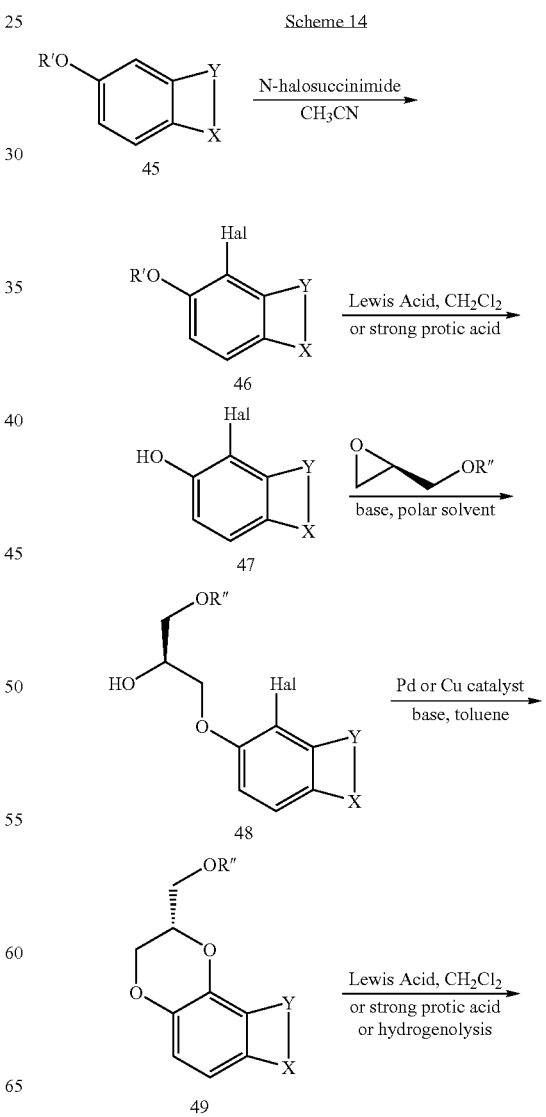

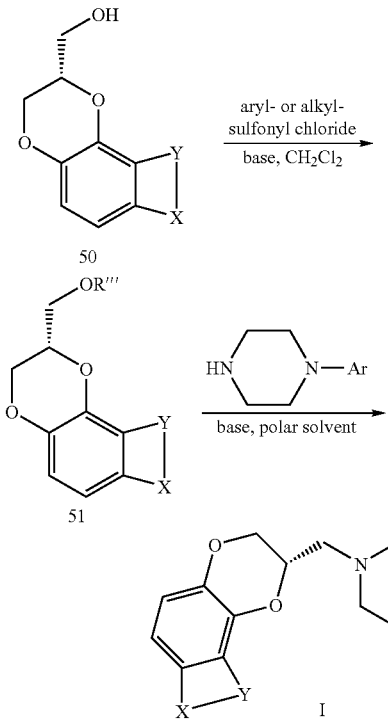

| Compound | 5-HT Transporter Affinity $K_i$ (nM) | $5HT_{1A}$ Receptor Affinity $K_i$ (nM) | $5HT_{1A}$ Function $IC_{50}$ (nM) ($I_{max}$) |
|---|---|---|---|
| Example 1 | 15.7 | 15.9 | 4564 (100) |
| Example 2 | 565 | 22.9 | 632 (26) |
| Example 3 | 76 | 1055? | nd |
| Example 4 | 34% @ 1 µM | 95% @ 1 µM | 994 (87) |
| Example 5 | 35.5 | 80% @ 1 µM | 1715 (84) |
| Example 6 | 0% @ 1 µM | 81% A1 µM | 3938 (37) |
| Example 7 | 1.20 | 91% @ 1 µM | 557 (71) |
| Example 8 | 21.6 | 31.4 | 3107 (100) |
| Example 9 | | | |
| Example 10 | 88.5 | 82.5 | 403 (98) |
| Example 11 | 85.5 | 18.2 | 345 (84) |
| Example 12 | 48.0 | 47.3 | 3002 (100) |
| Example 13 | 0.25 | 20.0 | 326 (70) |
| Example 14 | 0.65 | 214 | 74.7 (58) |
| Example 15 | 13.5 | 3.70 | 82.5 (87) |
| Example 16 | 266 | 28.5 | ND |
| Example 17 | 74.0 | 718 | ND |
| Example 18 | 16.0 | 40.3 | ND |
| Example 19 | 123 | 167 | 3000 (90) |
| Example 20 | 688 | 2.85 | 82.8 (92) |
| Example 21 | 32.8 | 5.53 | 867 (83.5) |
| Example 22 | 19.8 | 53.2 | 4539 (76) |
| Example 23 | 56% @ 1 µM | 7.21 | 129 (71) |
| Example 24 | 310 | 7.27 | 57 (58) |
| Example 25 | 67 | 4.74 | $EC_{50}$ = 1135($E_{max}$ = 67) |
| Example 26 | 407 | 25.1 | $EC_{50}$ = 700 ($E_{max}$ = 64) |
| Example 27 | 101 | 17.15 | 2412 (82) |
| Example 29 | 200 | 1.26 | 1325 (100) |
| Example 33 | 7.30 | 1.75 | 316 (92) |
| Example 34 | 1.09 | 2.04 | |

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plates® counter to quantify bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin $5HT_{1A}$ receptor was established by testing the claimed compound's ability to displace [$^3$H] 8-OH-DPAT (dipropylamino-tetralin) from the $5HT_{1A}$ serotonin receptor following a modification of the procedure of Hall et al., J. Neurochem. 44, 1685 (1985) which utilizes CHO cells stably transfected with human $5HT_{1A}$ receptors. The $5HT_{1A}$ affinities for the compounds of the invention are reported below as $K_i$'s.

Antagonist activity at $5HT_{1A}$ receptors was established by using a $^{35}$S-GTPγS binding assay similar to that used by Lazareno and Birdsall (Br. J. Pharmacol. 109:1120, 1993), in which the test compound's ability to affect the binding of $^{35}$S-GTPγS to membranes containing cloned human $5HT_{1A}$ receptors was determined. Agonists produce an increase in binding whereas antagonists produce no increase but rather reverse the effects of the standard agonist 8-OH-DPAT. The test compound's maximum inhibitory effect is represented as the $I_{max}$, while its potency is defined by the $IC_{50}$.

The results of the three standard experimental test procedures described in the preceding three paragraphs were as follows:

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive-compulsive disorders (including but not limited to trichotillomania), obsessive-compulsive spectrum disorders (including but not limited to autism), social anxiety disorder, generalized anxiety disorder, obesity, eating disorders such as anorexia nervosa and bulimia nervosa, vasomotor flushing, cocaine and alcohol addiction, sexual dysfunction (including but not limited to premature ejaculation), incontinence (including, but not limited to fecal incontinence, urge incontinence, overflow incontinence, passive incontinence, reflex incontinence, stress urinary incontinence urinary exertional incontinence and urinary incontinence), and pain (including, but not limited to migraine, chronic back pain, phantom limb pain, neuropathic pain such as diabetic neuropathy, and post herpetic neuropathy) and related illnesses. Moreover, the compounds of this invention have potent affinity for and antagonist activity at brain $5HT_{1A}$ serotonin receptors. Recent clinical trials employing drug mixtures (e.g., fluoxetine and pindolol) have demonstrated a more rapid onset of antidepressant efficacy for a treatment combining SSRI activity and $5HT_{1A}$ antagonism (Blier and Bergeron, 1995; F. Artigas, et al., 1996; M. B. Tome, et al., 1997). The compounds of the invention are thus exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methylcellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions that are sterile solutions or suspensions can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

"Provide," as used herein, means either directly administering a compound or composition of the present invention, or administering a prodrug, derivative or analog which will form an equivalent amount of the active compound or substance within the body.

The present invention includes prodrugs of compounds of Formula I and Ia. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). *Design and Application of Prodrugs, Textbook of Drug Design and Development*, Chapter 5, 113–191 (1991), Bundgaard, et al., *Journal of Drug Deliver Reviews*, 8:1–38(1992), Bundgaard, *J. of Pharmaceutical Sciences*, 77:285 et seq. (1988); and Higuchi and Stella (eds.) *Prodrugs as Novel Drug Delivery Systems*, American Chemical Society (1975).

The following examples illustrate the production of representative compounds of this invention.

Intermediate 1

5-Bromo-6-Methoxy-2-Methylquinoline

A solution of 6-methoxy-2-methylquinoline (177 g, 1.02 mol) in acetonitrile (1.77 L) was cooled to 0–3° C. followed by portion-wise addition of N-bromo-succinimide (200 g, 1.12 mol) over a period of 30 minutes while maintaining the same temperature. The resulted brown slurry was warmed to ambient temperature and stirred for an additional 6 hours. The reaction was then quenched by a 10% NaHSO$_3$ solution (211 mL). The reaction mixture was concentrated to a volume of 600 mL then slowly poured into 0.1 N NaOH (2.5 L). The slurry (pH=9) was stirred at room temperature for 1 hour then filtered, washed with water (2×1 L) and dried in a vacuum oven to give 253 g (98.6%) of the title compound as a brown solid: R$_f$=0.39 (3:7) EtOAc:heptane; $^1$H NMR (DMSO) δ 8.30 (d, J=6.5 Hz, 1H), 7.98 (d, J=6.9 Hz, 1H), 7.70 (d, J=7.0 Hz, 1H), 7.47 (d, J=6.5 Hz, 1H), 4.02 (s, 3H), 2.66 (s, 3H).

Elemental Analysis for: $C_{11}H_{10}NOBr$ Calc'd: C, 52.40; H, 3.97; N, 5.56. Found: C, 52.13; H, 3.94; N, 5.61.

Intermediate 2

5-Bromo-2-Methyl-6-Quinolinol Hydrobromide

A mixture of 5-bromo-2-methyl-6-methoxyquinoline (30 g, 0.12 mol) in 48% HBr (135 mL) was heated to reflux for 7 hours then cooled to 5° C. in 1 hour to give a brown and thick slurry. The slurry was stirred at 0–5° C. for 1 hour then filtered, washed with EtOAc (2×50 mL) and dried in a vacuum oven to give 34.9 g (92%) of the title compound as a brown solid: $^1$H NMR (DMSO) δ 8.26 (d, J=8.7 Hz, 1H), 7.85 (d, J=9.1 Hz, 1H), 7.56 (d, J=9.1 Hz, 1H), 7.45 (d, J=8.7 Hz, 1H), 2.64 (s, 3H); $^{13}$C NMR (DMSO) δ 155.7, 152.0, 142.8, 133.3, 128.9, 126.4, 123.3, 121.2, 103.3, 24.1.

Intermediate 3

5-Bromo-2-Methyl-6-Quinolinol

A slurry of the hydrobromide salt of 5-bromo-2-methyl-6-quinolinol (3.4 g, 10.5 mmol) and Amberlyst A-21 ion-exchange resin (1.7 g, pre-washed with MeOH then dried in oven) in MeOH (35 mL) was stirred at room temperature for 3 hours. The mixture was then filtered and concentrated in vacuo to give 2.5 g (100%) of a yellow solid: $R_f$=0.36(1:1) EtOAc:heptane; $^1$H NMR (DMSO) δ 8.26 (d, J=8.4 Hz, 1H), 7.82 (d, J=9.3 Hz,1H), 7.47 (t, J=9.1 Hz, 2H), 2.66 (s, 3H).

Intermediate 4

(2S)-1-(Benzyloxy)-3-[(5-Brom-2-Methyl-6-Quinolinyl)Oxyl]-2-Pr Pan I

A solution of 5-bromo-2-methyl-6-quinolinol (30.1 g, 126 mmol), (R)-benzyl glycidyl ether (24.9 g, 152 mmol) and triethylamine (17.4 g, 172 mmol) in DMA (200 mL) was heated in a 95–98° C. oil bath for 2 days. The solution was cooled and poured into water (300 mL) while stirring. The tan precipitate formed was filtered, washed with water (100 mL) and dried in a vacuum oven to give 37 g (73%) of the title compound as a tan solid: $R_f$=0.35 (EtOAc); $^1$H NMR (DMSO) δ 8.31 (d, J=8.8 Hz, 1H), 7.96 (d, J=9.2 Hz, 1H), 7.72 (d, J=9.3 Hz, 1H), 7.74 (d, J=8.7 Hz, 1H), 7.25–7.36 (m, 5H), 5.28 (d, J=5.1 Hz, 1H), 4.56 (s, 2H), 4.22–4.29 (m, 2H), 4.08–4.15 (m, 1H), 3.61–3.73 (m, 2H), 2.66 (s, 3H); [α]$_D$=+6.2° (c=1, CH$_3$OH).

Elemental Analysis for: $C_{20}H_{20}BrNO_3$ Calc'd: C, 59.66; H, 4.97; N, 3.48. Found: C, 59.43; H, 4.97; N, 3.55.

Intermediate 5

(2S)-2[(Benzyloxy)methyl]-8-methyl-2,3-Dihydro[1,4]Dioxino[2,3-f]Quinoline

A solution of (2S)-1-(benzyloxy)-3-[5-bromo-2-methyl-6-quinolinyl)oxyl]-2-propanol (10 g, 24.9 mmol), potassium phosphate tribasic (11.4 g, 50 mmol), Pd(OAc)$_2$ (280 mg, 1.25 mmol) and racemic BINAP (1.55 g, 2.49 mmol) in toluene (50 mL) was heated in a 100–102° C. oil bath for 3 d. The solution was cooled to room temperature then EtOAc (50 mL) and water (50 mL) were added. The reaction mixture was filtered through a bed of celite. The two layers were separated. The aqueous layer was extracted with EtOAc (30 mL). The combined organic layers were dried over Na$_2$SO$_4$, filtered and concentrated in vacuo to give 8 g (100%) of the crude product as a brown syrup. The crude product can be carried through the debenzylation step before purification. A sample of the crude mixture was purified on SiO$_2$, eluted with (3:1) hexane:EtOAc gave the title compound as a yellow oil which solidified upon standing: $R_f$=0.5 (EtOAc); $^1$H NMR (DMSO) δ 8.24 (d, J=8.6 Hz, 1H), 7.46 (d, J=9.2 Hz, 1H), 7.27–7.38 (m, 7H); [α]$_D$=+7.9° (c=1.2, CHCl$_3$).

Elemental Analysis for: $C_{20}H_{19}NO_3$ Calc'd: C, 74.68; H, 5.91; N, 4.36. Found: C, 74.48; H, 6.03; N, 4.14.

Intermediate 6

[(2S)-8-Methyl-2,3-Dihydro[1,4]Dioxino[2,3-f]Quinolin-2-yl]Methanol

To a solution of (2S)-2[(benzyloxy)methyl-8-methyl-2,3-dihydro[1,4]dioxino[2,3-f]quinoline (0.16 g, 0.5 mmol) in EtOH (1 mL) was added cyclohexene (0.5 mL) then 10% Pd/C (0.016 g, 10 mol %). The mixture was heated to reflux under N$_2$ for 18 hours then cooled and filtered. The catalyst was rinsed with methanol and the filtrate was concentrated in vacuo to afford 0.113 g (98%) of the title alcohol as an off-white solid: $^1$H NMR (CD$_3$OD) δ 8.46 (m, 1H), 7.47 (m, 1H), 7.38–7.31 (m, 2H), 4.40 (m, 1H), 4.36 (m, 1H), 4.18 (m, 1H), 3.91 (m, 2H), 2.68 (s, 3H).

Intermediate 7

[(2R)-8-Methyl-2,3-Dihydro[1,4]Dioxino[2,3-f]Quinolin-2-yl]Methyl 4-Bromobenzenesulfonate A solution of [(2S)-8-methyl-2,3-dihydro[1,4]dioxino[2,3-f]quinolin-2-yl]-methanol (4.0 g, 17.3 mmol), brosyl chloride (4.86 g, 19.0 mmol), dimethylamino pyridine (20 mg, 0.16 mmol) and triethylamine (3.62 mL, 25.8 mmol) in toluene (40 mL) was stirred at 60° C. for 6 hours. The reaction mixture was cooled to room temperature then water (20 mL) was added. After 30 minutes, the two layers were separated. The organic layer was extracted with 8% NaHCO$_3$ (20 mL) and H$_2$O (20 mL), dried over Na$_2$SO$_4$, filtered and concentrated in vacuo. The solid obtained was dissolved in isopropyl alcohol (50 mL) and toluene (10 mL) at 80° C., cooled to room temperature over 1 hour then filtered, washed with (5:1) IPA:toluene (2×5 mL) and dried in a vacuum oven to give 5.99 g (76.9%) of the title compound as an off-white solid: $^{13}$C NMR (CDCl$_3$) δ 157.9, 144.3, 138.1, 134.7, 132.9, 129.7, 129.6, 129.0, 122.4, 121.7, 121.3, 118.8, 70.7, 67.6, 64.5, 25.4

Intermediate 8

[(2R)-8-Methyl-2,3-Dihydro[1,4]Dioxino[2,3-f]Quinolin-2-yl]Methyl 4-Methylbenzenesulfonate A solution of [(2S)-8-methyl-2,3-dihydro[1,4]dioxino[2,3-f]quinolin-2-yl]-methanol (0.13 g, 0.57 mmol), tosyl chloride (0.16 g, 0.82 mmol) and triethylamine (0.65 mL, 4.7 mmol) in CH$_2$Cl$_2$ (8 mL) was stirred at room temperature for 18 hours. CHCl$_3$ (30 mL) and H$_2$O (30 mL) were added. The two layers were separated. The aqueous layer was extracted with CHCl$_3$ (20 mL). The combined organic layers were dried over Na$_2$SO$_4$, filtered and concentrated in vacuo. Purification on SiO$_2$, eluting with (1:1) hexane:EtOAc gave 0.19 g (88%) of the title compound as a brown syrup: mp 115–117° C.; $^1$H NMR (CDCl$_3$) δ 8.12 (d, J=8.6 Hz, 1H), 7.76 (m, 2H), 7.51 (d, J=9 Hz, 1H), 7.20–7.60 (m, 4H), 4.5–4.6 (m, 1H), 4.2–4.4 (m, 3H), 4.1–4.2 (m, 1H), 2.70 (s, 3H), 2.39 (s, 3H);

$^{13}$C NMR (DMSO) δ 156.9, 145.4, 143.6, 137.9, 134.7, 132.2, 130.4, 128.7, 128.0, 121.8, 121.6, 121.3, 121.3, 118.3, 70.9, 68.6, 64.1, 60.1, 24.9, 21.4, 21.1, 14.4.

EXAMPLE 1

(2S)-2-{[4-(3-chlorophenyl)piperazin-1-yl]methyl}-8-methyl-2,3-dihydro[1,4]dioxino[2,3-f]quinoline A mixture of [(2R)-8-methyl-2,3-dihydro[1,4]dioxino[2,3-f]quinolin-2-yl]methyl 4-bromobenzenesulfonate (647 mg, 1.44 mmol), 3-chlorophenyl-piperazine hydrochloride (1.0 g, 4.3 mmol) and diisopropylethylamine (0.75 mL, 4.3 mmol) in anhydrous DMSO (6 mL) were heated at 50° C. overnight. The cooled reaction mixture was diluted with saturated aqueous sodium bicarbonate (10 mL) and extracted with ethyl acetate (3×10 mL). The combined organic layers were washed with brine (3×30 mL), dried over MgSO$_4$, filtered, and concentrated in vacuo. Flash chromatography on silica gel (5% MeOH/CH$_2$Cl) afforded 280 mg (68%) of the desired product as a beige solid: mp 110–112° C.; MS (ESI) m/z nnn [M+H]$^+$.

Elemental Analysis for: C$_{23}$H$_{24}$ClN$_3$O$_2$.0.2 H$_2$O Calc'd: C, 66.81; H, 5.95; N, 10.16. Found: C, 66.68; H, 6.02; N, 10.20.

EXAMPLE 2

(2S)-2-{[4-(4-chlorophenyl)piperazin-1-yl]methyl}-8-methyl-2,3-dihydro[1,4]dioxino[2,3-f]quinoline To a mixture of [(2R)-8-methyl-2,3-dihydro[1,4]dioxino[2,3-f]quinolin-2-yl]methyl 4-bromobenzenesulfonate (577 mg, 1.28 mmol) and 4-chlorophenylpiperazine dihydrochloride (1.03 g, 3.81 mmol) in anhydrous DMSO (10 mL) was added N,N-diisopropylethylamine (1.33 mL, 3.81 mmol). The reaction mixture was heated at 75° C. overnight. The cooled reaction mixture was diluted with saturated aqueous sodium bicarbonate solution (50 mL) and extracted with ethyl acetate (3×50 mL). The combined organic layers were dried over MgSO$_4$, filtered, and concentrated in vacuo. Flash chromatography on silica gel (50% hexanes/EtOAc) afforded 260 mg (15%) of the title compound as a tan solid: MS EI m/z 410.09 [M+H]$^+$.

Elemental Analysis for: C$_{23}$H$_{24}$ClN$_3$O$_2$.0.67 H$_2$O.0.13 C$_4$H$_8$O$_2$ Calc'd: C, 65.18; H, 6.13; N, 9.69. Found: C, 65.56; H, 6.09; N, 9.29.

EXAMPLE 3

(2S)-2-{[4-(3,4-dichlorophenyl)piperazin-1-yl]methyl}-8-methyl-2,3-dihydro[1,4]dioxine[2,3-f]quinoline

[(2R)-8-methyl-2,3-dihydro[1,4]dioxino[2,3-f]quinolin-2-yl]methyl 4-methylbenzene-sulfonate (0.41 g, 1.1 mmole) and 1-(3,4-dichlorophenyl)-piperazine (0.26 g, 1.1 mmole) were combined in 3 mL of DMSO. This solution was stirred at 100° C. under nitrogen for 5.5 hours. The reaction was cooled to room temperature. The solvent was evaporated at reduced pressure. The residue was partitioned between ethyl acetate and saturated aqueous sodium bicarbonate. The organic phase was washed twice with water, dried over magnesium sulfate and concentrated in vacuum to give 0.61 g of oil. The crude residue was column chromatographed on silica gel using a gradient of ethyl acetate and hexane to give 0.17 g of the title compound as a yellow oil. This was dissolved in EtOH and fumaric acid (0.05 g, 0.4 mmole) was added. Filtration gave 0.100 g of the title compound as a tan solid: mp 140–144° C.; MS (ESI) m/z 444 [M+H]$^+$.

Elemental Analysis for: C$_{23}$H$_{23}$Cl$_2$N$_3$O$_2$.0.5 C$_4$H$_4$O$_4$.0.75 H$_2$O Calc'd: C, 58.20; H, 5.18; N, 8.14. Found: C, 58.35; H, 5.01; N, 7.75.

EXAMPLE 4

(2S)-2-{[4-(2-methoxyphenyl)piperazin-1-yl]methyl}-8-methyl-2,3-dihydro[1,4]dioxino[2,3-f]quinoline A mixture of [(2R)-8-methyl-2,3-dihydro[1,4]dioxino[2,3-f]quinolin-2-yl]methyl 4-bromobenzenesulfonate (783 mg, 1.74 mmol) and 2-methoxyphenyl piperazine (1.0 g, 5.22 mmol) in anhydrous DMSO (10 mL) were heated at 70° C. overnight. The reaction was quenched with the addition of saturated aqueous sodium bicarbonate (50 mL) and extracted with EtOAc (3×50 mL). The combined organic layers were dried over MgSO$_4$, filtered, and concentrated in vacuo. Flash chromatography on silica gel (50% EtOAc/hexanes) afforded 420 mg (60%) of the desire product as a white foam: mp 44–47° C.; MS (ESI) m/z 406 [M+H]$^+$.

Elemental Analysis for: C$_{24}$H$_{27}$N$_3$O$_3$.0.22 H$_2$O.0.06 C$_4$H$_8$O$_2$ Calc'd: C, 70.20; H, 6.79; N, 10.13. Found: C, 70.51; H, 6.87; N, 9.73.

EXAMPLE 5

(2S)-2-{[4-(3-methoxyphenyl)piperazin-1-yl]methyl}-8-methyl-2,3-dihydro[1,4]dioxino[2,3-f]quinoline A mixture of [(2R)-8-methyl-2,3-dihydro[1,4]dioxino[2,3-f]quinolin-2-yl]methyl 4-bromobenzenesulfonate (702 mg, 1.56 mmol) and 3-methoxyphenyl piperazine (890 mg, 4.63 mmol) in anhydrous DMSO (10 mL) were heated at 65° C. overnight. The cooled reaction mixture was diluted with saturated aqueous sodium bicarbonate (50 mL) and extracted with ethyl acetate (3×50 mL). The combined organic layers were dried over MgSO$_4$, filtered, and concentrated in vacuo. Flash chromatography on silica gel (50% EtOAc/hexanes) afforded 560 mg (88%) of the desired product as a white solid: mp 90–91° C.; MS (ESI) m/z 406 [M+H]$^+$.

Elemental Analysis for: C$_{24}$H$_{27}$N$_3$O$_3$.0.72 H$_2$O Calc'd: C, 68.89; H, 6.85; N, 10.04. Found: C, 68.51; H, 6.79; N, 9.87.

EXAMPLE 6

(2S)-2-{[4-(4-methoxyphenyl)piperazin-1-yl]methyl}-8-methyl-2,3-dihydro[1,4]dioxino[2,3-f]quinoline This compound was prepared as described for Example 5, using 4-methoxyphenyl piperazine (880 mg, 4.58 mmol) and 742 mg (1.65 mmol) of [(2R)-8-methyl-2,3-dihydro[1,4]dioxino[2,3-f]quinolin-2-yl]methyl 4-bromobenzene-sulfonate, to afford 560 mg (84%) of the title compound as a white solid: mp 164–165° C.; MS (ESI) m/z406 [M+H]$^+$.

Elemental Analysis for: C$_{24}$H$_{27}$N$_3$O$_3$ Calc'd: C, 71.09; H, 6.71; N, 10.36. Found: C, 70.87; H, 6.81; N, 10.29.

EXAMPLE 7

(2S)-2-{[4-(dihydrobenzo[1,4]dioxin-5-yl)piperazin-1-yl]methyl}-8-methyl-2,3-dihydro[1,4]dioxino[2,3-f]quinoline This compound was prepared as described for Example 5, using 1-(2,3-dihydro-1,4-benzodioxan-5-yl)-piperazine (710 mg, 3.22 mmol) and 534 mg (1.19 mmol) of [(2R)-8-methyl-2,3-dihydro[1,4]dioxino[2,3-f]quinolin-2-yl]methyl 4-bromo-benzenesulfonate, to afford 480 mg (93%) of the title compound as a yellow oil. The fumarate salt was generated using 0.9 eq of fumaric acid to yield 302 mg of a beige solid: mp 154–155° C.; MS (ESI) m/z434.16 [M+H]$^+$.

Elemental Analysis for: $C_{25}H_{27}N_3O_4 \cdot 0.5\ C_4H_4O_4 \cdot 0.72\ H_2O$ Calc'd: C, 64.28; H, 6.08; N, 8.33. Found: C, 63.89; H, 5.97; N, 8.06.

EXAMPLE 8

(2S)-8-methyl-2-[4-(3-trifluoromethyl-phenyl)piperazin-1-ylmethyl]-2,3-dihydro[1,4]dioxine[2,3-f]quinoline A mixture of [(2R)-8-methyl-2,3-dihydro[1,4]dioxino[2,3-f]quinolin-2-yl]methyl 4-bromobenzenesulfonate (652 mg, 1.45 mmol) and 3-trifluoromethylpiperazine (0.82 mL, 4.34 mmol) in anhydrous DMSO (5 mL) were heated at 50° C. for 2 days. The cooled reaction mixture was diluted with saturated aqueous sodium bicarbonate (10 mL) and extracted with ethyl acetate (3×10 mL). The combined organic layers was washed with brine (3×30 mL), dried over MgSO$_4$, filtered, and concentrated in vacuo. Flash chromatography on silica gel (70% EtOAc/hexanes) afforded 580 mg (90%) of the title compound as a white solid: mp 123–124° C.; MS EI m/z444.13 [M+H]$^+$.

Elemental Analysis for: $C_{24}H_{24}F_3N_3O_2$ Calc'd: C, 65.00; H, 5.45; N, 9.48. Found: C, 64.99; H, 5.52; N, 9.39.

EXAMPLE 9

(2S)-8-methyl-2-[4-(3-fluorophenyl)piperazin-1-yl]methyl]-2,3-dihydro[14]dioxine[2,3-f]quinoline This compound was prepared as described for Example 8, using 1-(3-fluorophenyl)-piperazine (1.35 g, 7.49 mmol), and 1.12 g (2.5 mmol) of [(2R)-8-methyl-2,3-dihydro[1,4]dioxino[2,3-f]quinolin-2-yl]methyl 4-bromobenzene-sulfonate in 10 mL of DMSO, to afford 0.95 g (97%) of the title compound as an orange-brown solid: mp 133–135° C.; MS (ESI) m/z394 [M+H]$^+$.

Elemental Analysis for: $C_{23}H_{24}FN_3O_2$ Calc'd: C, 70.21; H, 6.15; N, 10.68. Found: C, 70.24; H, 6.24; N, 10.65.

EXAMPLE 10

(2S)-2-{[4-(2,3-dimethylphenyl)piperazin-1-yl]methyl}-8-methyl-2,3-dihydro[1,4]dioxino[2,3-f]quinoline A mixture of 1-(2,3-dimethylphenyl)-piperazine (1.13 g, 5.94 mmol) and [(2R)-8-methyl-2,3-dihydro[1,4]dioxino[2,3-f]quinolin-2-yl]methyl 4-bromobenzene-sulfonate (871 mg, 1.93 mmol) in anhydrous DMSO (10 mL) was heated overnight at 70° C. The reaction was diluted with saturated aqueous sodium bicarbonate (50 mL) and extracted with EtOAc (3×50 mL). The combined organic layers were dried over MgSO$_4$, filtered, and concentrated in vacuo. Flash chromatography on silica gel (50% EtOAc/hexanes) afforded 700 mg (90%) of the title compound as a white solid: mp 112–113° C.; MS (ESI) m/z 404 [M+H]$^+$.

Elemental Analysis for: $C_{25}H_{29}N_3O_2$ Calc'd: C, 74.41; H, 7.24; N, 10.41. Found: C, 73.98; H, 7.15; N, 10.34.

EXAMPLE 11

(2S)-2-{[4-(3,4-dimethylphenyl)piperazin-1-yl]methyl}-8-methyl-2,3-dihydro[1,4]dioxino[2,3-f]quinoline This compound was prepared as described for Example 10, using 1-(3,4-dimethylphenyl)-piperazine (1.01 g, 5.33 mmol), and 804 mg (1.79 mmol) of [(2R)-8-methyl-2,3-dihydro[1,4]dioxino[2,3-f]quinolin-2-yl]methyl 4-bromobenzene-sulfonate, to afford 404 mg (68%) of the title compound as a white foam: mp 118–120° C.; MS (ESI) m/z404 [M+H]$^+$.

Elemental Analysis for: $C_{25}H_{29}N_3O_2$ Calc'd: C, 74.41; H, 7.24; N, 10.41. Found: C, 74.19; H, 7.05; N, 10.29.

EXAMPLE 12

(2S)-8-methyl-2-[(4-quinolin-2-ylpip razin-1-yl) methyl]-2,3-dihydro[1,4]dioxino[2,3-f]quinoline A solution of [(2R)-8-methyl-2,3-dihydro[1,4]dioxino[2,3-f]quinolin-2-yl]methyl 4-bromobenzenesulfonate (0.34 g, 0.75 mmol), 2-(1-piperazinyl) quinoline (0.46 g, 1.38 mmole), and 0.34 mL of triethylamine (0.34 mL, 2.4 mmol) in dimethyl sulfoxide (30 mL) was heated under nitrogen at 90° C. for 12 hours. The cooled reaction mixture was poured into water (100 ml) and extracted with methylene chloride (3×100 ml). The organic layer was washed with water (3×150 ml), dried over anhydrous sodium sulfate, filtered and the solvent was removed under vacuum. Flash chromatography on silica gel (1/44/55 methanol/ethyl acetate/hexanes) afforded 0.15 g (21%) of a light brown oil. The oil was dissolved in ethyl acetate and made into its hydrochloride salt using excess ethereal hydrochloric acid, to give 0.07 g of an orange-brown solid: mp 237–243° C.

Elemental Analysis for: $C_{26}H_{26}FN_4O_2 \cdot 0.50\ H_2O \cdot 4.0\ HCl$ Calc'd: C, 53.72; H, 5.37; N, 9.64. Found: C, 54.04; H, 5.82; N, 9.84.

EXAMPLE 13

(2S)-8-methyl-2-{4-(6-nitroquinolin-2-yl)piperazin-1-yl]methyl)-2,3-dihydro[1,4]dioxino[2,3-f]quinoline A solution of [(2R)-8-methyl-2,3-dihydro[1,4]dioxino[2,3-f]quinolin-2-yl]methyl 4-bromobenzenesulfonate (0.44 g, 0.97 mmol), 6-nitro-2-piperazin-1-yl-quinoline (0.3 g, 1.2 mmol) and triethylamine (0.2 ml, 1.9 mmol) in dimethylsulfoxide (40 ml) was heated at 90° C. under nitrogen for 12 hours. The reaction mixture was poured into water (100 ml) and extracted with methylene chloride (3×100 ml). The organic layer was washed with water (3×150 ml), dried over anhydrous sodium sulfate, filtered and the solvent was removed under vacuum. The crude oil was column chromatographed on silica gel (2.5% methanol-ethyl acetate). The product-containing fractions were concentrated under vacuum to give 0.22 g (48%) of the title compound as a orange foam. The hydrogen chloride salt was prepared in ethyl acetate and collected as a yellow solid: mp: 200° C. (dec).

Elemental Analysis for: $C_{26}H_{25}N_5O_4$. 2.75HCl Calc'd: C, 54.62; H, 4.89; N, 12.25. Found: C, 54.97; H, 4.91; N, 12.38.

EXAMPLE 14

(2S)-8-methyl-2-{4-(6-chloroquinolin-2-yl)piperazin-1-yl]methyl)-2,3-dihydro[1,4]dioxino[2,3-f] quinoline This compound was prepared by the same method as for Example 13, using 6-chloro-2-piperazin-1-yl-quinoline (0.60 g, 2.42 mmole), 0.55 g (1.2 mmol) of [(2R)-8-methyl-2,3-dihydro[1,4]dioxino[2,3-f]quinolin-2-yl]methyl 4-bromobenzene-sulfonate, and 0.34 mL (2.4 mmol) of triethylamine in dimethyl sulfoxide (36 mL), to afford 0.38 g (69%) of a light yellow oil after chromatography. The oil was dissolved in ethyl acetate and made into its hydrochloride salt using hydrochloric acid in ether in excess to give 0.08 g of orange crystals: m.p. 209–218° C.

Elemental Analysis for: $C_{26}H_{25}ClN_4O_2.0.50H_2O.4.0$ HCl.0.05 $C_4H_8O_2$ Calc'd: C, 47.30; H, 5.36; N, 8.42. Found: C, 47.67; H, 5.43; N, 8.93.

EXAMPLE 15

2-(4-{[(2S)-8-methyl-2,3-dihydro[1,4]dioxino[2,3-f] quinolin-2-yl]methyl}piperazin-1-yl}quinoline-6-carbonitrile This compound was prepared by the same method as for Example 13, using 6-cyano-2-piperazin-1-yl-quinoline (0.30 g, 1.26 mmole), 0.28 g (0.63 mmol) of [(2R)-8-methyl-2,3-dihydro[1,4]dioxino[2,3-f]quinolin-2-yl]methyl 4-bromobenzene-sulfonate, and 0.18 mL (1.3 mmol) of triethylamine in dimethyl sulfoxide (36 mL), to afford 0.38 g (%) of a colorless oil after chromatography. The oil was dissolved in ethyl acetate and made into its hydrochloride salt using excess ethereal hydrochloric acid to give 0.04 g of a grayish powder: m.p. 213–241° C.

Elemental Analysis for: $C_{27}H_{25}N_5O_2$.3.0 HCl.0.25$H_2O$.0.30 $C_4H_8O_2$ Calc'd: C, 57.23; H, 5.26; N, 11.83. Found: C, 57.11; H, 5.66; N, 11.66.

EXAMPLE 16

(2S)-2-{[4-(7-methoxy-1-benzofuran-3-yl)-1-piperazinyl]methyl}-8-methyl-2,3-dihydro[1,4]dioxino[2,3-f]quinoline Step 1: To a stirred solution of $TiCl_4$ (1 M solution in $CH_2Cl_2$, 32 ml) and 7-methoxy-benzofuran-3-one (5.0 g, 30.5 mmol) in methylene chloride (200 ml) at −10° C., ethyl-1-piperazine carboxylate (18.96 g, 120 mmol) was slowly added. After the addition, the reaction mixture was warmed to room temperature and slowly refluxed for 24 hrs. After cooling to room temperature, the reaction was quenched with 2 N aqueous HCl. The organic layer was separated and the aqueous layer was extracted with chloroform. The combined organic layers were washed well with water and dried over anhydrous $MgSO_4$, then filtered and concentrated. The brown residue was triturated with diethyl ether and the separated brown solid was filtered and air-dried. The product was pure enough and taken to next step without further purification. Yield: 8.3 g, (90%); Mp 121° C.; MS (ESI) m/z305 [M+H]$^+$.

Step 2: 4-(7-Methoxy-benzofuran-3-yl)-piperazine-1-carboxylic acid ethyl ester obtained in step 1, (7.0 g, 23 mmol) was dissolved in 95% ethanol and 3 N aqueous NaOH (25 ml) was added. The reaction mixture was refluxed for 24 hrs. At the end, the reaction mixture was concentrated and extracted with chloroform. The combined organic layers were washed well with brine, then were dried over anhydrous $MgSO_4$, filtered and concentrated. The brown oil was pure enough to take on to the next step without purification. Yield: 5.0 g (93%); MS (ESI) m/z233 [M+H]$^+$.

Step 3: A mixture of 1-(7-methoxy-benzofuran-3-yl)-piperazine obtained from the step 2 (232 mg, 1 mmol) and [(2R)-8-methyl-2,3-dihydro[1,4]dioxino[2,3-f]quinolin-2-yl]methyl 4-methylbenzenesulfonate (385 mg, 1 mmol) and diisopropyl ethyl amine (5 ml, excess) was heated at 120° C. for 24 hrs. At the end, the reaction mixture was poured into water and extracted with chloroform. The combined organic layers were washed well with water, then were dried over anhydrous $MgSO_4$, filtered and concentrated. Flash chromatography on $SiO_2$ (50% ethyl acetate/hexane the 90% ethyl acetate/hexane afforded 89 mg (20%) of the title compound as a yellow spongy solid: mp 56° C.; MS (ESI), m/z446 [M+H]; $^1$H NMR (CDCl$_3$): δ 8.27 (d, 1H), 7.64 (d, 1H), 7.3–7.1 (m, 5H), 6.9 (d, 1H), 4.55–4.40 (m, 2H), 4.1–4.2 (m, 1H), 4.0 (s, 3H), 3.5 (t, 1H), 3.2–3.2 (m, 4H), 2.9–2.7 (m, 5H), 2.7 (s, 3H).

EXAMPLE 17

(2S)-2-{[4-(5-fluoro-1-benzofuran-3-yl)-1-piperazinyl]methyl}-8-methyl-2,3-dihydro[1,4]dioxino[2,3-f]quinoline Step 1: Following the procedure outlined in Example 16, Step 1, 4-(5-fluoro-benzofuran-3-yl)-piperazine-1-carboxylic acid ethyl ester was prepared from 5-fluoro-benzofuran-3-one (3.0 g 19.7 mmol), $TiCl_4$ (1 M solution in $CH_2Cl_2$, 7.0 ml) and ethyl-1-piperazine carboxylate (3.9 g, 25 mmol). Yield: 3.5 g (60%) of a brown oil: MS (ESI) m/z 293 [M+H]$^+$.

Step 2: Following the procedure outlined in Example 16, Step 2, 1-(5-fluoro-benzofuran-3-yl)-piperazine was prepared from 4-(5-fluoro-benzofuran-3-yl)-piperazine-1-carboxylic acid ethyl ester (3.0 g 10.2 mmol) and 3 N aqueous NaOH (25 ml). Yield: 800 mg (35%) of a brown oil: MS (ESI) m/z 221 [M+H]$^+$.

Step 3: Following the procedure outlined in Example 16, Step 3, (2S)-2-{[4-(5-fluoro-1-benzofuran-3-yl)-1-piperazinyl]methyl}-8-methyl-2,3-dihydro[1,4]dioxino-[2,3-f] quinoline was prepared starting from 1-(5-fluoro-benzofuran-3-yl)-piperazine (220 mg, 1 mmol) and [(2R)-8-methyl-2,3-dihydro[1,4]dioxino[2,3-f]quinolin-2-yl]methyl 4-methylbenzenesulfonate (385 mg, 1 mmol). The product was purified by silica gel column chromatography (80% ethyl acetate/hexane). The HCl salt was prepared by dissolving the free base in 10% methanolic HCl, to afford a green solid. Yield: 160 mg (36%); MS (ESI) m/z 434 [M+H]$^+$; $^1$H NMR (d$_6$-DMSO): δ 11.97 (bs, 1H), 9.3 (bs, 1H), 8.0–8.5 (m, 7H), 7.2 (t, 1H), 5.2 (bs, 1H), 4.6-3-0 (complex multiplet, 12H), 2.9 (s, 3H).

EXAMPLE 18

(2S)-2-{[4-(1-benzofuran-3-yl)-1-piperazinyl]methyl}-8-methyl-2,3-dihydro[1,4]dioxino[2,3-f]quinoline Step 1: Following the procedure outlined in Example 16, Step 1, 4-(benzofuran-3-yl)-piperazine-1-carboxylic acid ethyl ester was prepared starting from benzofuran-3-one (10.0 g 74.6 mmol), TiCl$_4$ (1 M solution in CH$_2$Cl$_2$, 60 ml) and ethyl-1-piperazine carboxylate (48 g, 303 mmol). Yield: 16 g (78%) of a brown oil; MS (ESI) m/z275 [M+H]$^+$.

Step 2: Following the procedure outlined in Example 16, Step 2, 1-(benzofuran-3-yl)-piperazine was prepared starting from 4-(benzofuran-3-yl)-piperazine-1-carboxylic acid ethyl ester (15.0 g, 54.7 mmol) and 3 N aqueous NaOH (50 ml). Yield: 6.0 g (54%) of a brown oil: MS (ESI) m/z203 [M+H]$^+$.

Step 3: Following the procedure outlined in Example 16, Step 3, (2S)-2-{[4-(1-benzofuran-3-yl)-1-piperazinyl]methyl}-8-methyl-2,3-dihydro[1,4]dioxino[2,3-f]quinoline was prepared starting from 1-(benzofuran-3-yl)-piperazine (404 mg, 2 mmol) and [(2R)-8-methyl-2,3-dihydro[1,4]dioxino[2,3-f]quinolin-2-yl]methyl 4-methylbenzenesulfonate (770 mg, 2 mmol). The product was purified by silica gel chromatography (60% ethyl acetate/hexane). Yield: 150 mg (18%); MS (ESI) m/z 416 [M+H]$^+$; $^1$H NMR (CDCl$_3$): δ 8.3 (d, 1H), 7.2–7.9 (m, 8H), 4.5–4.7 (m, 2H), 4.1 (m,1H), 3.3–2.7 (m, 10H), 2.6 (s, 3H).

EXAMPLE 19

(2S)-8-methyl-2-{[(2S)-2-methyl-4-quinolin-2-ylpiperazin-1-yl]methyl}-2,3-dihydro[1,4]dioxino[2,3-f]quinoline A mixture of [(2R)-8-methyl-2,3-dihydro[1,4]dioxino[2,3-f]quinolin-2-yl]methyl 4-bromobenzenesulfonate (0.165 g, 0.367 mmol) and (S)-2-(3-methyl-piperazin-1-yl)-quinoline (250 mg, 1.10 mmol) in anhydrous dimethylsulfoxide (4 mL) was heated at 50° C. overnight. The cooled reaction was diluted with saturated aqueous sodium bicarbonate (20 mL) and extracted with ethyl acetate (3×20 mL). The combined organic layers were washed with brine (30 mL), dried over anhydrous sodium sulfate, filtered, and concentrated in vacuo. Flash chromatography on silica gel (2/2/96 methanol/2 M ammonia in methanol/methylene chloride) afforded 100 mg (62%) of the title compound as an off-white solid: mp 141–144° C.; MS (ES) m/z 441 [M+H]$^+$; [α]$_D$ –36.5° (c 1.0, DMSO).

Elemental Analysis for: C$_{27}$H$_{28}$N$_4$O$_2$.0.2H$_2$O Calc'd: C, 73.02; H, 6.45; N, 12.61. Found: C, 72.91; H, 6.74; N, 12.52.

EXAMPLE 20

2-((3R)-3-methyl-4-{[(2S))-8-methyl-2,3-dihydro[1,4]dioxino[2,3-f]quinolin-2-yl]methyl}piperazin-1-yl]quinoline-6-carbonitrile A mixture of [(2R)-8-methyl-2,3-dihydro[1,4]dioxino[2,3-f]quinolin-2-yl]methyl 4-bromobenzenesulfonate (476 mg, 1.06 mmol) and (R)-2-(3-methyl-piperazin-1-yl)-quinoline-6-carbonitrile (800 mg, 3.17 mmol) in anhydrous dimethylsulfoxide (11 mL) was heated at 50° C. overnight. The cooled reaction was diluted with saturated aqueous sodium bicarbonate (50 mL) and extracted with ethyl acetate (3×50 mL). The combined organic layers were washed with brine (70 mL), dried over anhydrous sodium sulfate, filtered, and concentrated in vacuo. Flash chromatography on silica gel (90/5/5 ethyl acetate/hexane/triethylamine) afforded 330 mg (67%) of the title compound as light yellow stable foam: MS (ES) m/z466 [M+H]$^+$; [α]$_D$ –34.0° (c 1.0, DMSO).

Elemental Analysis for: C$_{28}$H$_{27}$N$_5$O$_2$.0.4H$_2$O Calc'd: C, 71.14; H, 5.93; N, 14.81. Found: C, 71.00; H, 5.79; N, 14.59.

EXAMPLE 21

(2S)-8-methyl-2-{[(2R)-2-methyl-4-quinolin-2-ylpiperazin-1-yl]methyl}-2,3-dihydro[1,4]dioxino[2,3-f]quinoline A mixture of [(2R)-8-methyl-2,3-dihydro[1,4]dioxino[2,3-f]quinolin-2-yl]methyl 4-bromobenzenesulfonate (238 mg, 0.528 mmol) and (R)-2-(3-methyl-piperazin-1-yl)-quinoline (350 mg, 1.58 mmol) in anhydrous dimethylsulfoxide (6 mL) was heated at 50° C. overnight. The cooled reaction was diluted with saturated aqueous sodium bicarbonate (30 mL) and extracted with ethyl acetate (3×30 mL). The combined organic layers were washed with brine (50 mL), dried over anhydrous sodium sulfate, filtered, and concentrated in vacuo. Flash chromatography on silica gel (2/2/96 methanol/2 M ammonia in methanol/methylene chloride) afforded 110 mg (47%) of the title compound as an off-white solid: mp 78–82° C.; MS (ES) m/z441 [M+H]$^+$; [α]$_D$ –33.0° (c 1.0, DMSO)

Elemental Analysis for: C$_{27}$H$_{28}$N$_4$O$_2$.0.3H$_2$O Calc'd: C, 72.72; H, 6.46; N, 12.56. Found: C, 72.77; H, 6.40; N, 12.29.

EXAMPLE 22

(2S)-8-methyl-2-{[4-(2-naphthyl)piperazin-1-yl]methyl}-2,3-dihydro[1,4]dioxino[2,3-f]quinoline A mixture of [(2R)-8-methyl-2,3-dihydro[1,4]dioxino[2,3-f]quinolin-2-yl]methyl 4-bromobenzenesulfonate (2.73 g, 6.06 mmol) and 1-naphthalen-2-yl-piperazine (3.86 g, 18.2 mmol) in anhydrous dimethylsulfoxide (60 mL) was heated at 50° C. overnight. The cooled reaction was diluted with saturated aqueous sodium bicarbonate (200 mL) and extracted with ethyl acetate (3×200 mL). The combined organic layers were washed with brine (300 mL), dried over anhydrous sodium sulfate, filtered, and concentrated in vacuo. Flash chromatography on silica gel (2/2/95 methanol/ammonium hydroxide/methylene chloride) did not provide clean product. Re-chromatography on silica gel (90/5/5 ethyl acetate/hexane/triethylamine) afforded 1.80 g (69%) of the title compound as a beige solid: mg 134–137° C.; MS (ES) m/z426 [M+H]$^+$.

Elemental Analysis for: C$_{27}$H$_{27}$N$_3$O$_2$.0.1H$_2$O Calc'd: C, 75.89; H, 6.42; N, 9.83. Found: C, 75.69; H, 6.68; N, 9.96.

INTERMEDIATE

2-Pip razin-1-yl-quinolin-6-carboxylic acid amide

To a 0° C. solution of 6-cyano-2-piperazin-1-yl-quinoline (0.82 g, 3.5 mmol) and potassium carbonate (0.17 g, 12.1 mmol) in dimethyl sulfoxide (10 ml) was added hydrogen peroxide (30%, 1.3 ml). The mixture was stirred at 0° C. for 4 hours, then was quenched with saturated sodium hydrogen sulfite/sodium bicarbonate solution. The mixture was extracted with dichloromethane. The solvent was removed under vacuum. The mixture was adsorbed onto silica gel and chromatograph on silica gel (20/2/78 methanol/ammonium hydroxide/ethyl acetate). The product-containing fractions were concentrated under vacuum to give 0.67 g of a light yellow oil. The oil was dissolved in ethyl acetate and treated with excess ethereal hydrochloric acid to give the hydrochloride salt as an off-white solid: mp 295–298° C.

Elemental Analysis for: $C_{14}H_{16}N_4O.1.5\ HCl.0.25H_2O$ Calc'd: C, 53.30; H, 5.75; N, 17.76. Found: C, 53.09; H, 5.67; N, 18.00.

EXAMPLE 23

(2S)-2-[4–8-methyl-2,3-dihydro-[1,4]dioxino[2,3-f]quinolin-2-yl)-piperazin-1-yl]-quinoline-6-carboxylic acid amide A solution of (2R)-4-bromobenzenesulfonic acid 2,3-dihydro-[1,4]dioxino[2,3-f]quinolin-2-ylmethyl ester (0.56 g, 1.2 mmol) and triethylamine (0.26 ml, 1.9 mmol) in 20 ml of dimethyl sulfoxide was heated under nitrogen at 90° C. for 18 hours. The mixture was quenched with 1 N aqueous sodium hydroxide and extracted with ethyl acetate. The organic layer was washed with water. The solvent was removed under vacuum. The mixture was then adsorbed onto silica get and chromatographed on silica gel (10/1/89 methanol/ammonium hydroxide ethyl acetate). The product-containing fractions were concentrated under vacuum to give 0.25 g of a colorless oil. The oil was dissolved in ethyl acetate and treated with excess ethereal hydrochloric acid to give 0.25 g of the hydrochloride salt as a yellow solid: m.p. decomposed at 290° C.

Elemental Analysis for: $C_{27}H_{27}N_5O_3.2\ HCl\ H_2O$ Calc'd: C, 57.86; H, 5.58; N, 12.50. Found: C, 57.64; H, 5.60; N, 12.14.

EXAMPLE 24

(2S)-2-[4-(2,3-Dihydro-[1,4]dioxino[2,3-f]quinolin-2-ylmethyl)-piperazin-1-yl]-quinoline-6-carbonitrile A solution of (2R)-toluene-4-sulfonic acid 2,3-dihydro-[1,4]dioxino[2,3-f]quinolin-2-ylmethyl ester (0.49 g, 1.4 mmol), 6-cyano-2-piperazin-1-yl-quinoline (0.32 g, 1.6 mmol) and triethylamine (0.28 ml, 2.0 mmol) in 20 ml of dimethyl sulfoxide was heated under nitrogen at 90° C. for 18 hours. The mixture was quenched with 1 N aqueous sodium hydroxide and extracted with methylene chloride. The organic layer was washed with water. The solvent was removed under vacuum. The mixture was adsorbed onto silica get and chromatographed on silica gel (2/54/44 methanol/ethyl acetate/hexane). The product-containing fractions were concentrated under vacuum to give 0.33 g of a colorless oil. The oil was dissolved in ethyl acetate and treated with excess ethereal hydrochloric acid to give 0.24 g of the hydrochloride sat as a yellow solid: mp decomposed at 205° C.

Elemental Analysis for: $C_{26}H_{23}N_5O_2.3\ HCl.2H_2O$ Calc'd: C, 53.57; H, 5.19; N, 12.01. Found: C, 53.29; H, 5.13; N, 11.72.

EXAMPLE 25

(2S)-2-[4-(8-Ethyl-2,3-dihydro-[1,4]dioxino[2,3-f]quinolin-2-ylmethyl)-piperazin-1-yl]-quinoline-6-carbonitrile A solution of (2R)-toluene-4-sulfonic acid 8-ethyl-2,3-dihydro-[1,4]dioxino[2,3-f]quinolin-2-ylmethyl ester (0.4 g, 1.0 mmol), 6-cyano-2-piperazin-1-yl-quinoline (0.24 g, 1.0 mmol) and triethylamine (0.218 ml, 1.5 mmol) in 20 ml of dimethyl sulfoxide was heated under nitrogen at 90° C. for 18 hours. The mixture was quenched with 1 N aqueous sodium hydroxide and extracted with methylene chloride. The organic layer was washed with water. The solvent was removed under vacuum. The mixture was adsorbed onto silica get and chromatographed on silica gel (2/54/44 methanol/ethyl acetate/hexane. The product-containing fractions were concentrated under vacuum to give 0.11 g of a clear oil. The oil was dissolved in ethyl acetate and treated with excess ethereal hydrochloric acid to give 0.12 g of the hydrochloric acid salt as a yellow solid: m.p. decomposed at 184° C.

Elemental Analysis for: $C_{28}H_{27}N_5O_2\ .3\ HCl.2H_2O.0.5\ C_4H_8O_2$ Calc'd: C, 55.01; H, 5.85; N, 10.69. Found: C, 55.16; H, 5.45; N, 10.77.

EXAMPLE 26

(2S)-2-[4-(2-Methyl-7,8-dihydro-1,6,9-trioxa-3-aza-cyclopenta[a]naphthalen-8-ylmethyl)-piperazin-1-yl]-quinoline-6-carbonitrile A solution of (2R)-toluene-4-sulfonic acid 2-methyl-7,8-dihydro-1,6,9-trioxa-3-aza-cyclopenta[a]naphthalen-8-ylmethyl ester (0.5 g, 1.3 mmol), 6-cyano-2-piperazin-1-yl-quinoline (0.31 g, 1.3 mmol) and triethylamine (0.28 ml, 2.0 mmol) in 20 ml of dimethyl sulfoxide was heated under nitrogen at 90° C. for 18 hours. The mixture was quenched with 1 N aqueous sodium hydroxide and extracted with methylene chloride. The organic layer was washed with water. The solvent was removed under vacuum. The mixture was adsorbed onto silica get and chromatographed on silica gel (2/54/44 methanol/ethyl acetate/hexane). The product-containing fractions were concentrated under vacuum to give 0.34 g of a clear oil. The oil was dissolved in ethyl acetate and treated with excess ethereal hydrochloric acid to give 0.26 g of the hydrochloride salt as a white powder: m.p. decomposed at 227° C.

Elemental Analysis for: $C_{25}H_{23}N_5O_3.2\ HCl.2H_2O$ Calc'd: C, 54.55; H, 5.31; N, 12.72. Found: C, 54.70; H, 5.01; N, 12.58.

EXAMPLE 27

(2S)-2-{[4-(6-Bromoquinolin-2-yl)piperazin-1-yl]methyl}-8-methyl-2,3-dihydro[1,4]dioxino[2,3-f]quinoline The title compound was prepared as per either general Scheme I or II.

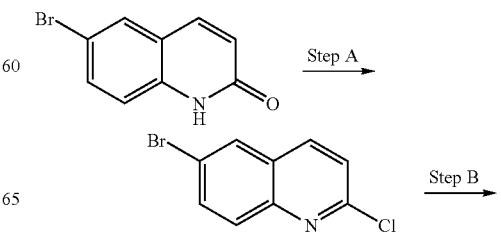

-continued

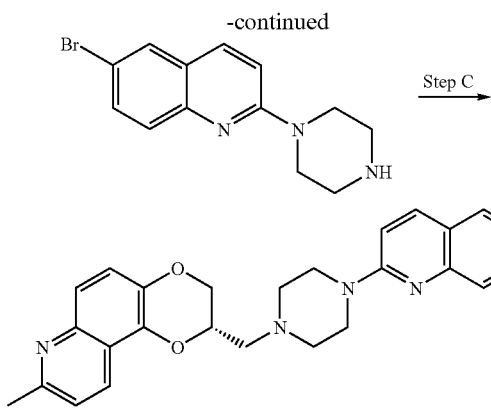

Step A. 6-Bromo-2-Chloroquinoline

A suspension of 6-bromo-3,4-dihydro-2-1H-quinolin-2-one (4.068 g, 18 mmol) and 2,3-dichloro-5,6-dicyano-1,4-benzoquinone (4.92 g, 21.6 mmol) in toluene (60 mL) is treated dropwise with phosphorous oxychloride (8.5 mL, 90 mmol). After heating for 2 hours at 92° C. the mixture is cooled, quenched with ice water, basified with 50% aqueous sodium hydroxide and extracted with ethyl acetate. The extracts are dried over anhydrous magnesium sulfate and evaporated. The residue is flash chromatographed on silica gel Merck-60 using a gradient of ethyl acetate (10–25%) in hexane to provide the title compound (4.27 g).

MS[(+)APCl, m/z]: 242.1 [M+H]$^+$ Anal. Calcd. For $C_9H_5BrClN$: C, 44.58; H, 2.08; N, 5.78. Found: C, 44.46; H, 2.04; N, 5.78.

Step B. 6-Bromo-2-piperazin-1-yl-quinoline

To a solution of 6-bromo-2-chloroquinoline of Step A (1.25 g, 5.15 mmol) in N,N-dimethylformamide (35 mL) is added piperazine (4.43 g, 51.4 mmol) and the mixture is heated at 110° C. under nitrogen for 3 hours. After cooling, it is diluted with saturated aqueous sodium bicarbonate and extracted with ethyl acetate. The extracts are dried over anhydrous magnesium sulfate and evaporated to dryness.

The residue is flash chromatographed on silica gel Merck-60 using a gradient of methanol (0–15%) in dichloromethane containing 0.2% ammonium hydroxide to provide the title compound as an off-white solid (1.3 g), m.p. 129–130° C.

MS [(+)ES, m/z]: 292.1 [M+H]$^+$ Anal. Calcd for $C_{13}H_{14}BrN_3$: C, 53.44; H, 4.83; N, 14.38. Found: C, 53.17; H, 4.81; N, 14.41.

Step C. (2S)-2-{[4-(6-Bromoquinolin-2-yl)piperazin-1-yl]methyl}-8-methyl-2,3-dihydro[1,4]dioxino[2,3-f]quinoline To a solution of [(2R)-8-methyl-2,3-dihydro[1,4]dioxino[2,3-f]quinolin-2-yl]methyl 4 bromobenzene sulfonate (2.31 g, 5.13 mmol) in dimethylsulfoxide (123 mL) is added the 6-bromo-2-piperazin-1-yl-quinoline of Step B (1.5 g, 5.13 mmol) and the mixture is heated at 75° C. under nitrogen overnight. The mixture is poured into saturated aqueous sodium bicarbonate and extracted with ethyl acetate. The extracts are dried over anhydrous magnesium sulfate and evaporated to dryness. The residue is flash chromatographed on silica gel Merck-60 using a gradient of methanol (0.5–2%) in ethyl acetate-hexane (55:45) to provide the title compound as an off-white solid (1.02 g), m.p. 153–154° C.

MS [(+)ES, m/z]: 505.1 (M+H]$^+$ Anal. Calcd. For $C_{26}H_{25}BrN_4O_2$: C, 61.79; H, 4.99; N, 11.09. Found: C, 62.24; H, 4.72; N, 10.71.

EXAMPLE 28

(2S)-2-{[4-(6-Bromoquinolin-2-yl)piperazin-1-yl]methyl}-8-methyl-2,3-dihydro[1,4]dioxino[2,3-f]quinoline Scheme II

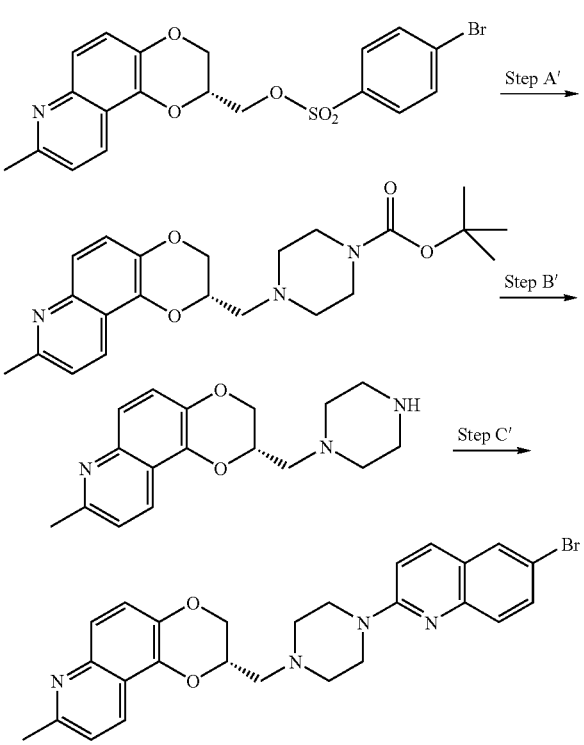

Step A'. (2S)-4-(8-Methyl-2,3-dihydro-[1,4]dioxino[2,3-f]quinolin-2-ylmethyl)-piperazine 1 carboxylic acid tert-butyl ester To a suspension of [(2R)-8-methyl-2,3-dihydro[1,4]dioxino[2,3-f]quinolin-2-yl]methyl-4-bromobenzene sulfonate (0.783 g, 1.74 mmol) is added N-Boc-piperazine (0.972 g, 5.22 mmol) in dimethylsulfoxide (10 mL), The mixture is heated at 75° C. under nitrogen for 4 hours, cooled, poured into saturated aqueous sodium bicarbonate and extracted with ethyl acetate. The extracts are dried over anhydrous magnesium sulfate and evaporated to dryness. The residue is flash chromatographed on silica gel Merck-60 using a gradient of ethyl acetate (20–50%) in hexane to provide the title compound as a colorless glass (0.635 g).

MS [(+)ES, m/z]: 400.2 [M+H]$^+$

Step B'. 0.8-Methyl-2-piperazin-1-ylmethyl-2,3-dihydro-[1,4]dioxino[2,3-f]quinoline To an ice-cold solution of (2S)-4-(8-methyl-2,3-dihydro-[1,4]dioxino[2,3-f]quinolin-2-ylmethyl)-piperazine 1 carboxylic acid tert-butyl ester of Step A' (0.550 g, 1.37 mmol) in ethyl acetate (8 mL) is added dropwise 1 M hydrochloric acid in diethyl ether (15 mL). The mixture is allowed to come to room temperature, diluted with methanol (10–15 mL) and warmed at 35° C. until the reaction is complete by TLC. The solvents are removed in vacuo and the residue is slurried in diethyl ether. The solid is collected and dried in vacuo. The free base is prepared by basifying an aqueous solution of the hydrochloride salt with concentrated aqueous sodium hydroxide, followed by extraction with dichloromethane. The title compound is obtained as a thick oil (quantitative yield).

MS [(+)ES, m/z]: 300.1 [M+H]$^+$

Step C'. (2S)-2-{[4-(6-Bromoquinolin-2-yl)piperazin-1-yl]methyl}-8-methyl-2,3-dihydro[1,4]dioxino[2,3-f]quinoline A mixture of 8-methyl-2-piperazin-1-ylmethyl-2,3-dihydro-[1,4]dioxino[2,3-f]quinoline of Step B' (0.493 g, 1.64 mmol) and 6-bromo-2-chloroquinoline of Example 1, Step A (0.507 g) is heated at 95° C. under nitrogen for 6 hours, followed by heating at 105° C. for 4 hours. The mixture is cooled, poured into saturated aqueous sodium bicarbonate and extracted with ethyl acetate. The extracts are dried over anhydrous magnesium sulfate and evaporated to dryness. The residue is flash chromatographed on silica Merck-60 using a gradient of methanol (0.5–2%) in dichloromethane-hexane (45:55), to provide the title compound (0.147 g) identical to the compound of Example 27, Step C.

EXAMPLE 29

The compound of Step B' of Scheme 2 can be alternatively, prepared in one step according to the following procedure

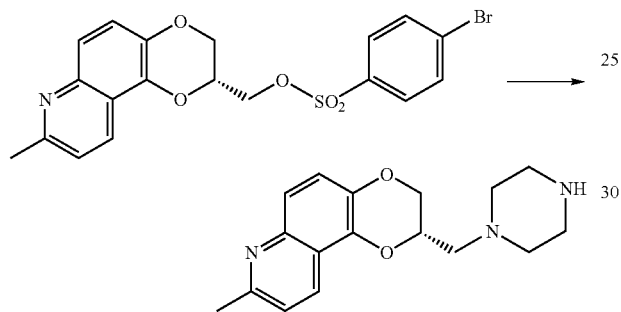

8-Methyl-2-piperazin-1-ylmethyl-2,3-dihydro-[1,4]dioxino[2,3-f]quinoline

A mixture of [(2R)-8-methyl-2,3-dihydro[1,4]dioxino[2,3-f]quinolin-2-yl]methyl-4-bromobenzene sulfonate (1.35 g, 3 mmol) and piperazine (2.58 g, 30 mmol) in dimethylsulfoxide (16 mL) is heated at 75° C. under nitrogen for 1 hour, cooled and poured into saturated aqueous sodium bicarbonate. The mixture is extracted with ethyl acetate and the extracts are dried over anhydrous magnesium sulfate and evaporated to dryness. The residue is flash chromatographed on silica gel Merck-60 using a gradient of methanol (5–25%) in dichloromethane containing 0.2% ammonium hydroxide to provide the title compound as an off-white oil (0.736 g) identical to the compound of example 1B, step B'.

EXAMPLE 30

(2S)-2-{[4-(6-methoxyquinolin-2-yl)piperazin-1-yl]methyl]-8-methyl-2,3-dihydro[1,4]dioxino[2,3-f]quinoline The title compound was prepared according to Scheme III.

Scheme III

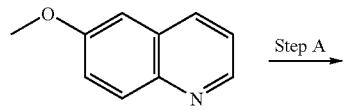

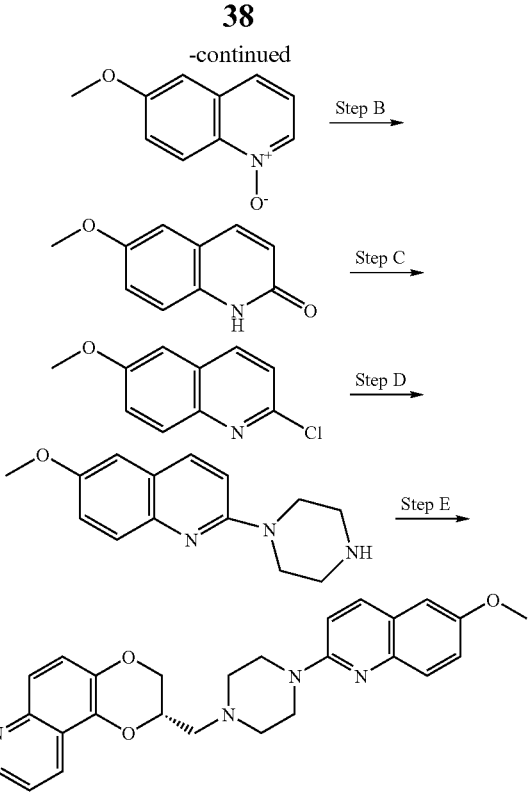

Step A. 6-Methoxyquinoline 1-oxide

A solution of 6-methoxyquinoline (11.21 g, 70 mmol) in glacial acetic acid is treated dropwise with 30% hydrogen peroxide (15 mL) and then heated at 82° C. for 19 hours. The reaction mixture is cooled, poured onto ice and carefully basified with concentrated ammonium hydroxide. The precipitate is collected, washed with hexane and dried in vacuo to provide the title compound (quantitative yield), which is used as such in the next step.

MS [(+)ES, m/z]: 176.1 [M+H]$^+$

Step B. 6-Methoxy-1H-quinolin-2-one

The crude 6-methoxyquinoline 1-oxide of Step A (70 mmol) is suspended in acetic anhydride (70 mL) and heated at 75° C. under nitrogen for 18 hours. The mixture is poured onto ice and carefully basified with ammonium hydroxide. The precipitate is collected, washed with hexane and dried. The solid is suspended in dichloromethane, filtered and dried to provide the title compound (5.136 g). Additional material (1.79 g) is obtained by flash chromatography of the mother liquors on silica gel Marck-60 using a gradient of methanol (1–5%) in hexane-ethyl acetate (1:1).

MS [(+)ES, m/z]: 176.1 [M+H]$^+$

Step C. 2-Chloro-6-methoxy-quinoline

A suspension of 6-methoxy-1H-quinolin-2-one of Step B (5.136 g, 29.2 mmol) in toluene (100 mL) is treated with phosphorous oxychloride 913.8 mL) and heated at 95° C. under nitrogen for 2 hours. The crude mixture is poured into ice water and basified with 50% aqueous sodium hydroxide. The solution is extracted with ethyl acetate, the extracts are dried over anhydrous magnesium sulfate and evaporated to dryness. The residue is pre-absorbed on silica gel Merck-60 and flash chromatographed using a gradient of ethyl acetate (10–20%) in hexane to provide the title compound (5.25 g) as a white crystalline solid, m.p. 105–107° C.

MS [(+)ES, m/z]: 194.04 [M+H]$^+$

Step D. 6-Methoxy-2-piperazin-1-yl-quinoline

To a solution of 2-chloro-6-methoxy-quinoline of Step C, (2.5 g, 12.91 mmol) in N,N-dimethylformamide (50 mL) is added piperazine (12 g) and the mixture is heated at 110° C. under nitrogen for 6 hours. The solution is diluted with saturated aqueous sodium bicarbonate and extracted with ethyl acetate. The extracts are dried over anhydrous magnesium sulfate and evaporated to dryness. The residue is flash chromatographed on silica gel Merck-60 using a gradient of methanol (4–10%) in dichloromethane containing 0.2% ammonium hydroxide to provide the title compound (1.6 g) as an off-white solid, m.p. 95–97° C.

MS [(+)ES, m/z]: 244.1 [M+H]+

Step E. (2S)-2-{[4-(6-methoxyquinolin-2-yl)piperazin-1-yl]methyl]-8-methyl-2,3-dihydro[1,4]dioxino[2,3-f]quinoline A mixture of 6-methoxy-2-piperazin-1-yl-quinoline of Step D (1.05 g, 4.31 mmol) in dimethylsulfoxide (15 mL) and [(2R)-8-methyl-2,3-dihydro[1,4]dioxino[2,3-f]quinolin-2-yl]methyl-4-bromobenzene sulfonate (1.62 g) is heated at 80° C. under nitrogen for 3 hours and at 90° C. for 1 additional hour. The solution is poured into saturated aqueous sodium bicarbonate and extracted with ethyl acetate. The extracts are dried over anhydrous magnesium sulfate and evaporated to dryness. The residue is flash chromatographed on silica gel Merck-60 using a gradient of methanol (0.5–3%) in dichloromethane-hexane (1:1) containing 0.1% ammonium hydroxide to provide the title compound (0.790 g). The pure material is charcoalized (in ethyl acetate), filtered, evaporated and induced to crystallize from hexane by sonication. The off-white solid melts at 158–160° C.

Calcd for $C_{27}H_{28}N_4O_3$ 0.3$H_2O$: C, 70.20; H, 6.24; N, 12.13. Found; C, 70.47; H, 6.95; N, 12.09. MS[(+)ES, m/z]: 457.1 [M+H]+

EXAMPLE 31

(2S)-2-{[4-(6-Trifluoromethoxyquinolin-2-yl)piperazin-1-yl]methyl]-8-methyl-2,3-dihydro[1,4]dioxino[2,3-f]quinoline The compound may be prepared according to Scheme IV.

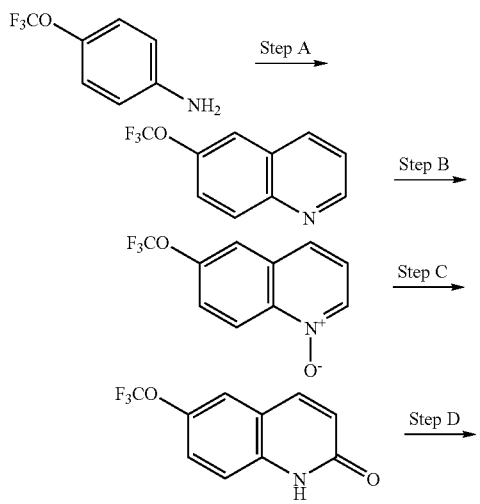

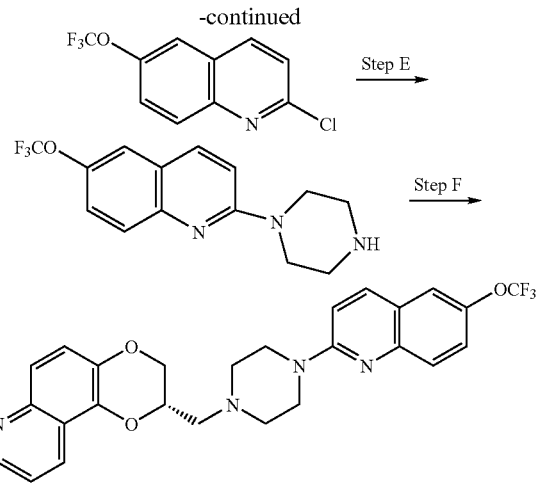

Step A. 6-Trifluoromethoxy-quinoline

A mechanically stirred mixture of 4-trifluoromethoxyaniline (8.85 g, 50 mmol), iron(II) sulfate heptahydrate (3 g), 3-nitrobenzene sulfonate sodium salt (16.85 g), boric acid (5 g) and glycerol (125 mL) is cooled in an ice bath and treated dropwise with concentrated sulfuric acid (30 mL). The mixture is then heated to 150° C. for 2 hours, cooled, poured onto ice and carefully basified with 50% aqueous sodium hydroxide. The mixture is repeatedly extracted with diethyl ether, the combined extracts are washed with brine, dried over anhydrous magnesium sulfate and evaporated to dryness (bath temperature below 32° C.). The residue is flash chromatographed on silica gel Merck-60 using dichloromethane to provide the title compound as a pale yellow oil, which is used as such in the next step.

MS [(+)ES, m/z]: 214.0 [M+H]+

Step B. 6-Trifluoromethoxy-quinoline 1-oxide

To a solution of the crude 6-trifluoromethoxy-quinoline of Step A (obtained from 50 mmol of 4-trifluoromethoxy aniline) in glacial acetic acid (54 mL) is added dropwise 30% hydrogen peroxide (8 mL). The mixture is heated at 82° C. under nitrogen for 16 hours, cooled, carefully basified with concentrated ammonium hydroxide and extracted with ethyl acetate. The extracts are washed with brine, dried over anhydrous magnesium sulfate and evaporated to dryness. The residue is twice azeotroped with benzene, and then flash chromatographed on silica gel Merck-60 using dichloromethane followed by a gradient of methanol (0.5–2%) in dichloromethane to provide the title compound as a pale brown oil that solidifies upon standing. The pale brown crystals (4.8 g) melt at 68–70° C.

MS [(+)ES, m/z]: 230.0 [M+H]+

Step C. 6-Trifluoromethoxy-1H-quinolin-2-one

A solution of 6-trifluoromethoxy-quinoline 1-oxide of Step B (4.58 g, 20 mmol) in acetic anhydride (20 mL) is heated at 135° C. under nitrogen for 4 hours. The mixture is poured onto ice, carefully basified with sodium carbonate and extracted with ethyl acetate. The extracts are washed with brine, dried over anhydrous magnesium sulfate and evaporated to dryness. The residue is flash chromatographed on silica Merck-60 using a gradient of methanol (0–3%) in hexane-ethyl acetate (1:1). The appropriate fractions are combined and evaporated. The residue is triturated with diethyl ether. The insoluble is collected, washed with hexane and dried to provide the title compound as a pale brown crystalline solid (1.086 g), m.p. 215–217° C.

MS [(+)ES, m/z]: 230.0 [M+H]+

Step D. 2-Chloro-6-trifluoromethoxy-quinoline

The title compound may be prepared in a manner analogous to Example 3, Step C, from the 6-trifluoromethoxy-1H-quinolin-2-one of Step C, and phosphorous oxychloride.

Step E. 2-Piperazin-1-yl-6-trifluoromethoxy-quinoline

The title compound is being prepared in a manner analogous to Example 3, Step D from the 2-chloro-6-trifluoromethoxy-quinoline of Step D and piperazine.

Step F. (2S)-2-{[4-(6-Trifluoromethoxyquinolin-2-yl)piperazin-1-yl]methyl]-8-methyl-2,3-dihydro[1,4]dioxino[2,3-f]quinoline The title compound may be prepared in a manner analogous to Example 3, Step E from the 2-piperazin-1-yl-6-trifluoromethoxy-quinoline of Step E and (2R)-8-methyl-2,3-dihydro[1,4]dioxino[2,3-f]quinolin-2-yl]methyl-4-bromobenzene sulfonate in dimethylsulfoxide.

EXAMPLE 32

2-[4-(6-Fluoro-quinolin-2-yl)-piperazin-1-ylmethyl]-8-methyl-2,3-dihydro-[1,4]dioxino[2,3-f]quinoline The compound may be prepared according to Scheme V.

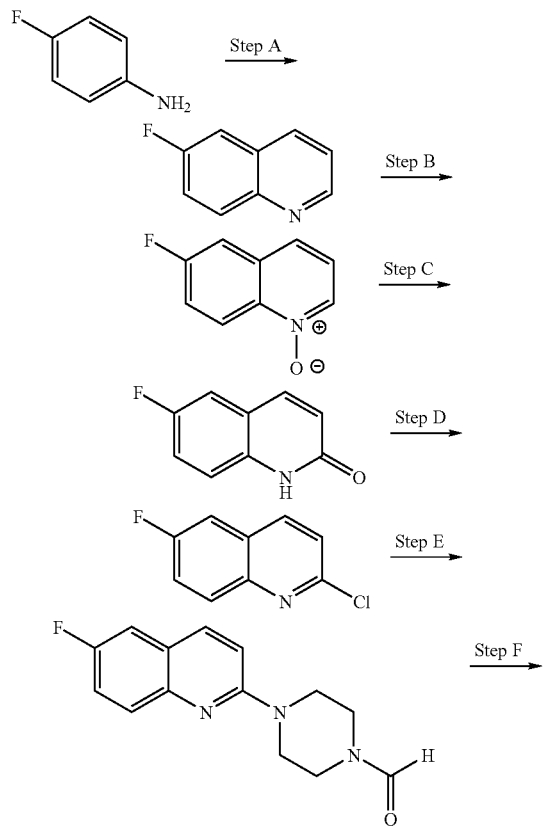

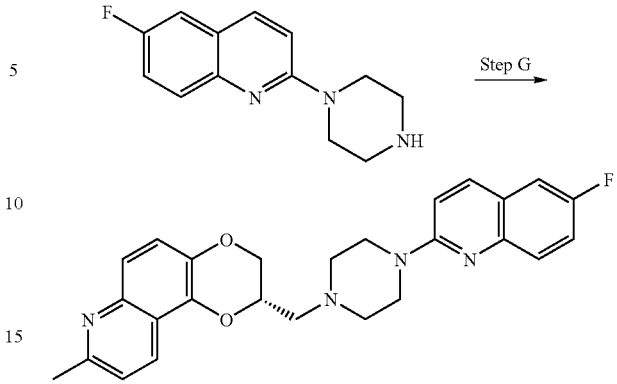

Step A. 6-Fluoroquinoline

A mechanically stirred mixture of 4-fluoro aniline (31 g, 279 mmol), iron(II) sulfate heptahydrate (9.4 g), nitrobenzene (19.6 g), boric acid (17 g), and glycerol (102 g) is cooled to ice bath temperature and treated dropwise with concentrated sulfuric acid (45 mL). The mixture is heated at 156° C. for 20 hours, then cooled in an ice bath and carefully basified with 50% aqueous sodium hydroxide. The mixture is repeatedly extracted with diethyl ether and then with dichloromethane. The combined extracts are washed with brine, dried over anhydrous magnesium sulfate, filtered, and evaporated to dryness (bath temperature below 30° C.). The residue is flash chromatographed on silica gel Merck-60 using a gradient of methanol (0–2%) in dichloromethane to provide the title compound as an oil (33 g), which is used without further purification.

Step B. 6-Fluoroquinoline 1-oxide

The 6-fluoroquinoline from Step A (6.0 g, 40.8 mmol) in glacial acetic acid (60 mL) is treated dropwise with hydrogen peroxide (14 mL) and heated with an oil bath to 78° C. overnight. The reaction mixture is concentrated at reduced pressure and the concentrate basified with solid sodium carbonate and extracted with dichloromethane. The extracts are dried over anhydrous magnesium sulfate, filtered, and concentrated to a light yellow solid (6.0 g). The residue is flash chromatographed on silica gel Merck-60 using a gradient of methanol (5–10%) in dichloromethane to provide the title compound as a white solid (0.99 g), m.p. 105–106° C.

MS [(+) ES, m/z]: 164.0 [M+H]+; Anal. Calcd for $C_9H_6FNO$: C, 66.26; H, 3.71; N, 8.59. Found: C, 66.09; H, 3.36; N, 8.65.

Step C. 6-Fluoroquinolin-2(1H)-one

A solution of 6-fluoroquinoline 1-oxide from Step B (5.0 g, 30.65 mmol) in acetic anhydride (30 mL) is heated at 110° C. for 6.5 hours. The reaction is allowed to stand at room temperature overnight. The solid (1.1 g) is collected and recrystallized from anhydrous ethanol (75 mL). The reddish crystals are collected by filtration and dried under high vacuum to give the title compound (0.653 g), m.p. dec. 269–270° C.

MS [(−)ES, m/z}: 162.0 (M−H)−

Step D. 2-Chloro-6-fluoroquinoline

A mixture of 6-fluoroquinolin-2(1H)-one from Step C, (0.971 g, 6 mmol), phosphorous oxychloride (2.83 mL, 30 mmol), and toluene (20 mL) is heated at 95° C. for 2 hours. The reaction is cooled in an ice bath and basified with 50% aqueous sodium hydroxide. The mixture is extracted with ethyl acetate and the extracts are dried over anhydrous magnesium sulfate, filtered, and concentrated to an orange solid (1.01 g). The residue is flash chromatographed on silica gel Merck-60 with 5% ethyl acetate in hexane to provide the title compound as a light pink solid, m.p. 99–101° C.

MS [EI, m/z]: 181 [M]$^+$Anal. Calcd for $C_9H_5ClFN$: C, 59.53; H, 2.78; N, 7.71. Found: C, 59.56; H, 2.79; N, 7.59.

Step E. 4-(6-Fluoroquinolin-2-yl)piperazine-1-carbaldehyde

A solution of 2-chloro-6-fluoroquinoline from Step D (0.8 g, 4.4 mmol) and piperazine (3.79 g, 44 mmol) in N,N-dimethylformamide (20 mL) is heated at 110° C. for 2 hours. The reaction is then basified with saturated aqueous sodium bicarbonate and extracted with ethyl acetate. The extracts are dried over anhydrous magnesium sulfate, filtered, and concentrated to give a tan oil. The oil is flash chromatographed on silica gel Merck-60 with a gradient of methanolic ammonia (5–10%) in ethyl acetate to provide the title compound (0.330 g) as an off-white solid, m.p. 110–111° C.

MS [(+) ES, m/z]: 260.1 [M+H]$^+$

Step F. 6-Fluoro-2-piperazin-1-yl-quinoline

The title compound may be prepared by treatment of 4-(6-fluoroquinolin-2-yl)piperazine-1-carbaldehyde of Step E with 4M sulfuric acid.

Step G. (2S)-2-{[4-(6-Fluoro-quinolin-2-yl)-piperazin-1-yl]methyl]-8-methyl-2,3-dihydro-[1,4]dioxino[2,3-f]quinoline The title compound is being prepared in a manner analogous to Example 3, Step E from the 6-fluoro-2-piperazin-1-yl-quinoline of Step F and (2R)-8-methyl-2,3-dihydro[1,4]dioxino[2,3-f]quinolin-2-yl]methyl-4-bromobenzene sulfonate in dimethylsulfoxide.

EXAMPLE 33

(2S)-2-{[4-(6-methoxyquinolin-2-yl)-1,4-diazepan-1-yl]methyl]-8-methyl-2,3-dihydro[1,4]dioxino[2,3-f]quinoline The title compound was prepared according to Scheme VI.

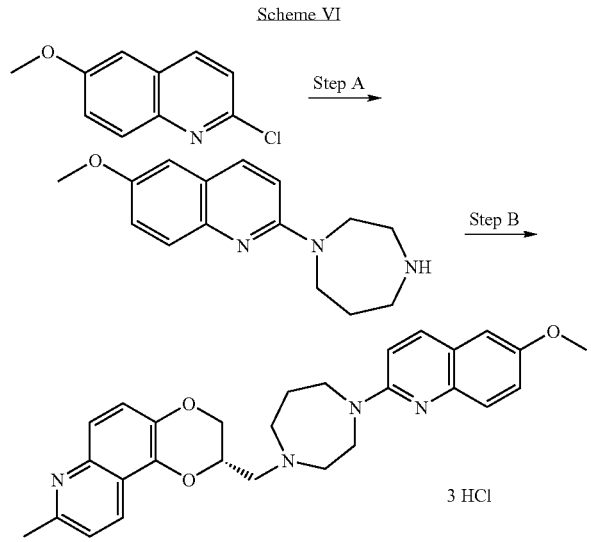

Scheme VI

Step A. 2-[1,4-Diazepan-2-yl-6-methoxy-quinoline

To a solution of 2-chloro-6-methoxy-quinoline (2.5 g, 12.91 mmol) in N,N-dimethylformamide (50 mL) is added homopiperazine (7.76 g, 77.46 mmol) and the mixture is heated at 110° C. under nitrogen for 6 hours. The solution is poured into saturated aqueous sodium bicarbonate and extracted with ethyl acetate. The extracts are dried over anhydrous magnesium sulfate and evaporated to dryness. The residue is flash chromatographed on silica gel Merck-60 using a gradient of methanol (2–10%) in dichloromethane containing 0.1% ammonium hydroxide to provide the title compound as a pale yellow syrup (1.54 g).

MS [(+)ES, m/z]: 258.2 [M+H]$^+$.

Step B. (2S)-2-{[4-(6-methoxyquin lin-2-yl)-1,4-diaz pan-1-yl]methyl]-8-m thyl-2,3-dihydro[1,4]di xino[2,3-f]quinolin A mixture of 2-[1,4-diazepan-2-yl-6-methoxy-quinoline of Step A (1.45 g, 5.66 mmol) and (2R)-8-methyl-2,3-dihydro[1,4]dioxino[2,3-f]quinolin-2-yl]methyl-4-bromobenzene sulfonate (3.1 g) in dimethylsulfoxide (15 mL) is heated at 75° C. under nitrogen for 9 hours. The reaction mixture is diluted with saturated aqueous sodium bicarbonate and extracted with ethyl acetate. The extracts are dried over anhydrous magnesium sulfate and evaporated to dryness. The residue is flash chromatographed on silica gel Merck-60 using a gradient of methanol (0.4–1.5%) in hexane-dichloromethane (1:1) containing 0.1% ammonium hydroxide to provide the title compound as a foam (0.800 g). The latter is dissolved in ethyl acetate, treated with charcoal, filtered, and treated with excess 1 M hydrochloric acid in diethyl ether. The mixture is evaporated and the residue triturated with cold diethyl ether. The insoluble is collected, washed with diethyl ether, and dried in vacuo to provide the hydrochloride salt of the title compound as a yellow solid, m.p. dec. around 238° C.

Anal. Calcd for $C_{28}H_{30}N_4O_3$ 3HCl 2 $H_2O$: C, 54.60; H, 6.05; N, 9.10. Found: C, 54.27; H, 5.68; N, 8.70. MS[(+)ES, m/z]: 471.2 [M+H]$^+$

EXAMPLE 34

2-(4-{[(2S)-8-Methyl-2,3-dihydro[1,4]dioxino[2,3-f]quinolin-2-yl]methyl}-1,4-diazepan-1-yl)quinoline-6-carbonitrile The title compound was prepared according to Scheme VII.

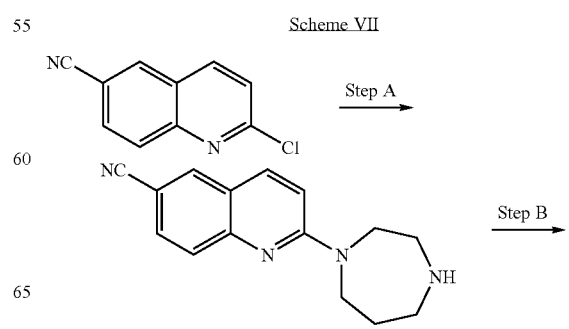

Scheme VII

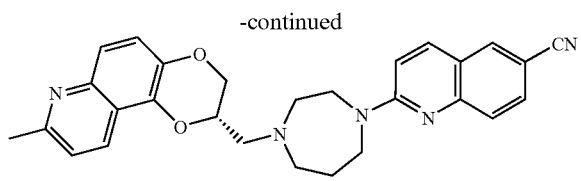

Step A. 2-(1,4-Diazepan-1-yl)quinoline-6-carbonitrile

A solution of 2-chloroquinoline-6-carbonitrile (2.0 g, 10.6 mmol) in N,N-dimethylformamide (50 mL) is heated to 50° C. under nitrogen. Homopiperazine (10.62 g, 106 mmol) is added and the solution is heated at 100° C. for 2.5 hours. The cold solution is poured into saturated aqueous sodium bicarbonate and extracted with ethyl acetate. The extracts are dried over anhydrous magnesium sulfate and concentrated to a light brown oil (3.44 g). The oil is flash chromatographed on silica Merck-60 eluting with a gradient of methanol (5–15%) in dichloromethane containing 0.2% ammonium hydroxide to provide the title compound (2.466) as a yellow waxy solid.

MS [(+) ES, m/z]; 253.2 ([M+H]$^+$

Step B. 2-(4-{[(2S)-8-Methyl-2,3-dihydro[1,4]dioxino[2,3-f]quinolin-2-yl]methyl}-1,4-diazepan-1-yl)quinoline-6-carbonitrile 2-(1,4-Diazepan-1-yl)quinoline-6-carbonitrile from Step A (1.0 g, 3.96 mmol) is taken up in dimethylsulfoxide (10 mL) and heated to 50° C. under nitrogen. (2R)-8-methyl-2,3-dihydro[1,4]dioxino[2,3-f]quinolin-2-yl]methyl-4-bromobenzene sulfonate (1.78 g, 3.96 mmol) is added, followed by triethylamine (0.58 mL, 4.16 mmol). The black solution is heated at 90° C. for 21 hours. 1 N, Sodium hydroxide is added to the cold reaction mixture, which is then extracted with dichloromethane. The extracts are dried over anhydrous magnesium sulfate, and concentrated to give a black oil. The oil is flash chromatographed on silica gel Merck-60 using 48% ethyl acetate/48% hexane/2% methanol to provide a tan oil (0.492 g). The material is further purified by prep HPLC, [Primeshere CN, 5×25 cm column, 8:2 dichloromethane-methanol gradient in heptane, flow rate 20 mL/min, detection at 254 nm, purity>99.9%] to give the title compound as an off white solid, m.p. 80–85° C.

MS [(+)ES, m/z]: 466.2 ([M+H]$^+$

EXAMPLE 35

(2S)-2-{[4-(6-Trifluoromethoxy-quinolin-2-yl)-1,4-diazepan-1-yl]methyl]-8-methyl-2,3-dihydro[1,4]dioxino[2,3-f]quinoline The title compound may be prepared according to Scheme VIII.

Scheme VIII

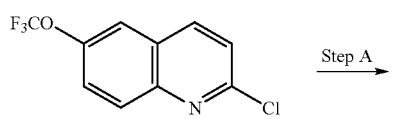

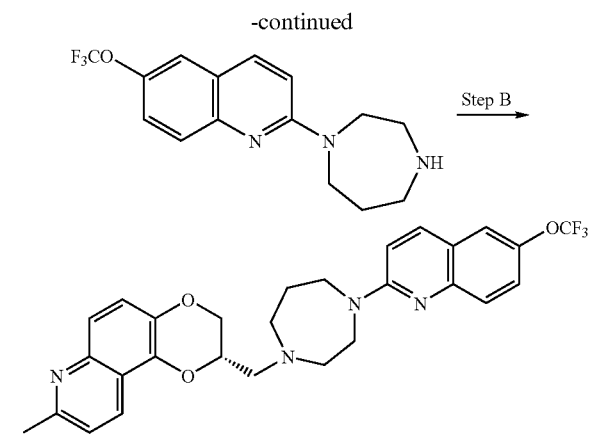

Step A. 2-[1,4-Diazepan-2-yl-6-trifluoromethoxy-quinoline

The title compound is being prepared in a manner analogous to Example 33, Step A from 2-chloro-6-trifluoromethoxy-quinoline and homopiperazine.

St p B. (2S)-2-{[4-(6-Trifluorom thoxyquin lin-2-yl)-1,4-diazepan-1-yl]methyl]-8-methyl-2,3-dihydro[1,4]dioxino[2,3-f]quinolin The title compound is being prepared in a manner analogous to Example 33, Step B from 2-[1,4-diazepan-2-yl-6-trifluoromethoxy-quinoline and (2R)-8-methyl-2,3-dihydro[1,4]dioxino[2,3-f]quinolin-2-yl]methyl-4bromobenzene sulfonate in dimethylsulfoxide.

EXAMPLE 36

2-[4-(6-Fluoro-quinolin-2-yl)-[1,4]diazepan-1-ylmethyl]-8-methyl-2,3-dihydro-[1,4]dioxino[2,3-f]quinoline The title compound may be prepared according to Scheme IX.

Scheme IX

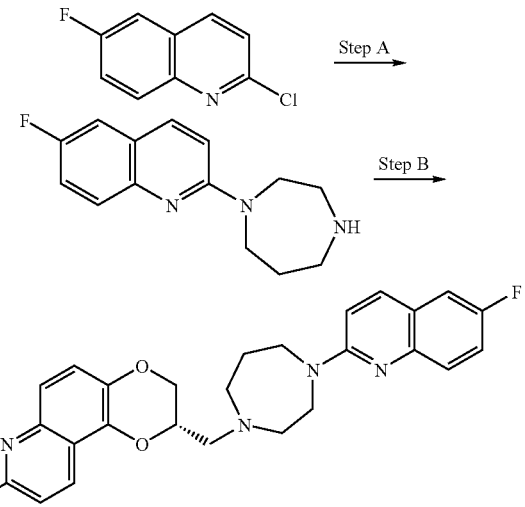

Step A. 6-Fluoro-2-[1,4]diazepan-1-yl-quinoline

The title compound may be prepared in analogous manner to Example 33, Step A from 2-chloro-6-fluoro-quinoline and homopiperazine St p B. 2-[4-(6-Fluoro-quinolin-2-yl)-[1,4]diaz pan-1-ylm thyl]-8-m thyl-2,3-dihydro-[1,4]dioxino[2,3-f]quin lin The title compound is being prepared in a manner analogous to Example 33, Step B from 6-fluoro-2-[1,4]diazepan-1yl-quinoline of Step A and (2R)-8-methyl-2,3-dihydro[1,4]dioxino[2,3-f]quinolin-2-yl]methyl-4-bromobenzene sulfonate in dimethylsulfoxide.

EXAMPLE 37

(2S)-2-{[4-(6-Bromo-quinolin-2-yl)-1,4-diazepan-1-yl]methyl}-8-methyl-2,3-dihydro[1,4]dioxino[2,3-f]quinoline The title compound may be prepared according to Scheme X.

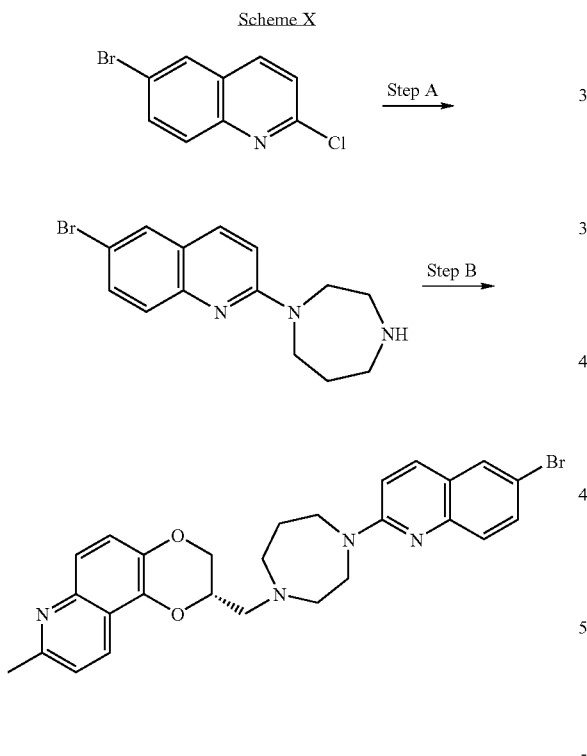

Step A. 6-Bromo-2-[1,4diazepan-1-yl-quinoline

The title compound may be prepared in a manner analogous to Example 33, Step A from 2-chloro-6-bromo-quinoline and homopiperazine.

St p B. 2-[4-(6-Bromo-quin lin-2-yl)-[1,4]diazepan-1-ylmethyl]-8-m thyl-2,3-dihydro-[1,4]dioxino[2,3-f]quinolin The title compound may be prepared in a manner analogous to Example 33, Step B from 6-bromo-2-[1,4]diazepan-1yl-quinoline of Step A and (2R)-8-methyl-2,3-dihydro[1,4]dioxino[2,3-f]quinolin-2-yl]methyl-4-bromobenzene sulfonate in dimethylsulfoxide.

EXAMPLE 38

8-Methyl-2-(4-quinolin-2-yl-[1,4]diazepan-1-ylmethyl)-2,3-dihydro-[1,4]dioxino[2,3-f]quinoline The compound may be prepared according to Scheme XI.

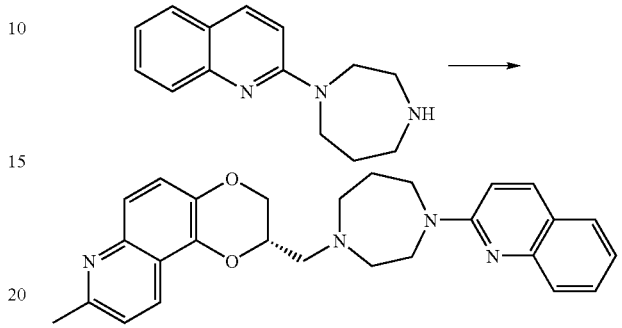

To a solution of 2-[1,4]-diazepan-1-yl-quinoline (Z)-2-butenedioate (20.5 g, 1.45 mmol) in dimethylsulfoxide (5 mL) is added (2R)-8-methyl-2,3-dihydro[1,4]dioxino[2,3-f]quinolin-2-yl]methyl-4-bromobenzene sulfonate (0.656 g, 1.456 mmol), followed by triethylamine (1.13 mL, 11.2 mmol). The mixture is heated at 80° C. under nitrogen for 17 hours, cooled, diluted ethyl acetate, basified with saturated aqueous sodium bicarbonate and extracted with ethyl acetate. The extracts are dried over anhydrous magnesium sulfate, and concentrated to give a brown oil. The oil is flash chromatographed on silica gel Merck-60 to provide the title compound.

EXAMPLE 39

8-M thyl-2-[4-(4-m thyl-quinolin-2-yl)-[1,4]di az pan-1-ylm thyl]-2,3-dihydro[1,4]dioxino[2,3-f]quinoline The compound may be prepared according to Scheme XII.

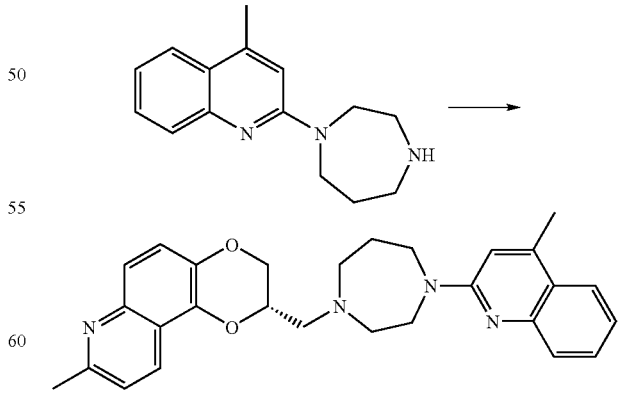

To a solution of 2-[1,4]diazepan-1-yl-4-methyl-quinoline (0.70 g, 1.478 mmol) in dimethylsulfoxide (5 mL) is added (2R)-8-methyl-2,3-dihydro[1,4]dioxino[2,3-f]quinolin-2-yl]methyl-4-bromobenzene sulfonate (0.600 g, 1.33 mmol), followed by triethylamine (0.618 mL, 4.4 mmol). The mixture is heated at 75° C. under nitrogen overnight, cooled, diluted ethyl acetate, basified with saturated aqueous sodium bicarbonate and extracted with ethyl acetate. The extracts are dried over anhydrous magnesium sulfate, and concentrated to give a brown oil. The oil is flash chromatographed on silica gel Merck-60 to provide the title compound.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:
1. A compound of formula I:

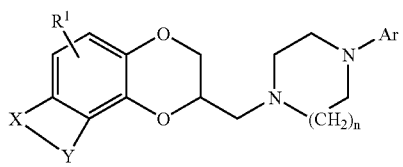

I wherein
  $R^1$ is hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
  the group X—Y is —N=C($R^2$)—C($R^3$)N—, —N=C($R^2$)—C($R^4$)=CH—, —N=C($R^2$)—N=CH—, —N=C($R^2$)—O—, or —NH—C($R^5$)=CH—;
  $R^2$ and $R^3$ are, independently, hydrogen, halo, amino, mono- or di-alkylamino in which each alkyl group has 1 to 6 carbon atoms or alkyl of 1 to 6 carbon atoms;
  $R^4$ is hydrogen or alkyl of 1 to 6 carbon atoms;
  $R^5$ is hydrogen, halo, trifluoromethyl, pentafluoroethyl or alkyl of 1 to 6 carbon atoms;
  Ar is phenyl, naphthyl, indolyl, indazolyl, thienyl, pyridinyl, pyrimidinyl, quinolinyl, benzofuranyl, benzothienyl, benzoisothiazolyl, or benzisoxazolyl, each optionally substituted with one to three substituents independently selected from hydroxy, halo, cyano, carboxamido, carboalkoxy of 2 to 6 carbon atoms, trifluoromethyl, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; and
  n is 1 or 2; or pharmaceutically acceptable salts thereof.

2. A compound according to claim 1, wherein $R^1$ is hydrogen, halo, cyano, trifluoromethyl, alkyl of 1 to 6 carbon atoms or alkoxy of 1 to 6 carbon atoms.

3. A compound according to claim 1, wherein $R^1$ is hydrogen, halo or alkoxy of 1 to 6 carbon atoms.

4. A compound according to claim 1, wherein $R^1$ is hydrogen.

5. A compound according to claim 1, wherein Ar is phenyl, quinolinyl, benzofuranyl, benzothienyl, or indolyl, each optionally substituted.

6. A compound according to claim 1, wherein X—Y is —N=C($R^2$)—C($R^4$)=CH— and $R^4$ is hydrogen or alkyl of 1 to 3 carbon atoms.

7. A compound according to claim 1, wherein $R^2$ and $R^3$ when present are independently selected from hydrogen, amino or alkyl of 1 to 6 carbon atoms.

8. A compound according to claim 1, wherein $R^2$ and $R^3$ when present are independently hydrogen or alkyl of 1 to 3 carbon atoms.

9. A compound according to claim 1, wherein $R^5$ is hydrogen, trifluoromethyl, pentafluoroethyl or alkyl of 1 to 6 carbon atoms.

10. A compound according to claim 1, wherein $R^5$ is hydrogen, trifluoromethyl or alkyl of 1 to 3 carbon atoms.

11. A compound according to claim 1, wherein said compound is (2S)-2-{[4-(3-chlorophenyl)piperazin-1-yl]methyl}-8-methyl-2,3-dihydro[1,4]dioxino[2,3-f]quinoline or a pharmaceutically acceptable salt thereof.

12. A compound according to claim 1, wherein said compound is (2S)-2-{[4-(4-chlorophenyl)piperazin-1-yl]methyl}-8-methyl-2,3-dihydro[1,4]dioxino[2,3-f]quinoline or a pharmaceutically acceptable salt thereof.

13. A compound according to claim 1, wherein said compound is (2S)-2-{[4-(3,4-dichlorophenyl)piperazin-1-yl[methyl}-8-methyl-2,3-dihydro[1,4]dioxine [2,3-f]quinoline or a pharmaceutically acceptable salt thereof.

14. A compound according to claim 1, wherein said compound is (2S)-2-{[4-(2-methoxyphenyl)piperazin-1-yl]methyl}-8-methyl-2,3-dihydro[1,4]dioxino[2,3-f]quinoline or a pharmaceutically acceptable salt thereof.

15. A compound according to claim 1, wherein said compound is (2S)-2-{[4-(3-methoxyphenyl)piperazin-1-yl]methyl-2,3}-8-methyl-2,3-dihydro[1,4]dioxino[2,3-f]quinoline or a pharmaceutically acceptable salt thereof.

16. A compound according to claim 1, wherein said compound is (2S)-2-{[4-(4-methoxyphenyl)piperazin-1-yl]methyl}-8-methyl-2,3-dihydro[1,4]dioxino[2,3-f]quinoline or a pharmaceutically acceptable salt thereof.

17. A compound according to claim 1, wherein said compound is (2S)-2-{[4-(dihydrobenzo[1,4]dioxin-5-yl)piperazin-1-yl]methyl}-8-methyl-2,3-dihydro[1,4]dioxino [2,3-f]quinoline or a pharmaceutically acceptable salt thereof.

18. A compound according to claim 1, wherein said compound is (2S)-8-methyl-2-[4-(3-trifluoromethyl-phenyl)piperazin-1-ylmethyl]-2,3-dihydro[1,4]dioxino[2,3-f]quinoline or a pharmaceutically acceptable salt thereof.

19. A compound according to claim 1, wherein said compound is (2S)-8-methyl-2-[4-(3-fluorophenyl)piperazin-1-ylmethyl]-2,3-dihydro[1,4]dioxino[2,3-f]quinoline or a pharmaceutically acceptable salt thereof.

20. A compound according to claim 1, wherein said compound is (2S)-2-{[4-(2,3-dimethylphenyl)piperazin-1-yl]methyl}-8-methyl-2,3-dihydro[1,4]dioxino[2,3-f]quinoline or a pharmaceutically acceptable salt thereof.

21. A compound according to claim 1, wherein said compound is (2S)-2-{[4-(3,4-dimethylphenyl)piperazin-1-yl]methyl}-8-methyl-2,3-dihydro[1,4]dioxino[2,3-f]quinoline or a pharmaceutically acceptable salt thereof.

22. A compound according to claim 1, wherein said compound is (2S)-8-methyl-2-[(4-quinolin-2-ylpiperazin-1-yl)methyl]-2,3-dihydro[1,4]dioxino[2,3-f]quinoline or a pharmaceutically acceptable salt thereof.

23. A compound according to claim 1, wherein said compound is ((2S)-8-methyl-2-{4-(6-nitroquinolin-2-yl)piperazin-1-yl]methyl)-2,3-dihydro [1,4]dioxino[2,3-f]quinoline or a pharmaceutically acceptable salt thereof.

24. A compound according to claim 1, wherein said compound is (2S)-8-methyl-2-{4-(6-chloroquinolin-2-yl)piperazin-1-yl]methyl)-2,3-dihydro[1,4]dioxino[2,3-f]quinoline or a pharmaceutically acceptable salt thereof.

25. A compound according to claim 1, wherein said compound is2-(4-{[(2S)-8-methyl-2,3-dihydro[1,4]dioxino[2,3-f]quinolin-2-yl]methyl}piperazin-1-yl}quinoline-6-carbonitrile or a pharmaceutically acceptable salt thereof.

26. A compound according to claim 1, wherein said compound is (2S)-2-{[4-(1-benzofuran-3-yl)-1-piperazinyl]methyl}-8-methyl-2,3-dihydro[1,4]dioxino[2,3-f]quinoline or a pharmaceutically acceptable salt thereof.

27. A compound according to claim 1, wherein said compound is (2S)-2-{[4-(5-fluoro-1-benzofuran-3-yl)-1-piperazinyl]methyl}-8-methyl-2,3-dihydro[1,4]dioxino[2,3-f]quinoline or a pharmaceutically acceptable salt thereof.

28. A compound according to claim 1, wherein said compound is ((2S)-2-{[4-(7-methoxy-1-benzofuran-3-yl)-1-piperazinyl]methyl}-8-methyl-2,3-dihydro[1,4]dioxino[2,3-f]quinoline or a pharmaceutically acceptable salt thereof.

29. A compound according to claim 1, wherein said compound is (2S)-8-methyl-2-{[(2S)-2-methyl-4-quinolin-2-ylpiperazin-1-yl]methyl}-2,3-dihydro[1,4]dioxino[2,3-f]quinoline or a pharmaceutically acceptable salt thereof.

30. A compound according to claim 1, wherein said compound is2-((3R)-3-methyl-4-{[(2S))-8-methyl-2,3-dihydro[1,4]dioxino[2,3-f]quinolin-2-yl]methyl}piperazin-1-yl]quinoline-6-carbonitrile or a pharmaceutically acceptable salt thereof.

31. A compound according to claim 1, wherein said compound is (2S)-8-methyl-2-{[(2R)-2-methyl-4-quinolin-2-ylpiperazin-1-yl]methyl}-2,3-dihydro[1,4]dioxino[2,3-f]quinoline or a pharmaceutically acceptable salt thereof.

32. A compound according to claim 1, wherein said compound is (2S)-8-methyl-2-{[4-(2-naphthyl)piperazin-1-yl]methyl}-2,3-dihydro[1,4]dioxino[2,3-f]quinoline or a pharmaceutically acceptable salt thereof.

33. A compound according to claim 1, wherein said compound is (2S)-2-[4-8-methyl-2,3-dihydro-[1,4]dioxino[2,3-f]quinolin-2-yl)-piperazin-1-yl]-quinoline-6-carboxylic acid amide or a pharmaceutically acceptable salt thereof.

34. A compound according to claim 1, wherein said compound is (2S)-2-[4-(2,3-Dihydro-[1,4]dioxino[2,3-f]quinolin-2-ylmethyl)-piperazin-1-yl]-quinoline-6-carbonitrile or a pharmaceutically acceptable salt thereof.

35. A compound according to claim 1, wherein said compound is (2S)-2-[4-(8-Ethyl-2,3-dihydro-[1,4]dioxino[2,3-f]quinolin-2-ylmethyl)-piperazin-1-yl]-quinoline-6-carbonitrile or a pharmaceutically acceptable salt thereof.

36. A compound according to claim 1, wherein said compound is (2S)-2-[4-(2-Methyl-7,8-dihydro-1,6,9-trioxa-3-aza-cyclopenta[a]naphthalen-8-ylmethyl)-piperazin-1-yl]-quinoline-6-carbonitrile or a pharmaceutically acceptable salt thereof.

37. A compound according to claim 1, wherein said compound is (2S)-2-{[4-(6-Bromoquinolin-2-yl)piperazin-1-yl]methyl}-8-methyl-2,3-dihydro[1,4]dioxino[2,3-f]quinoline or a pharmaceutically acceptable salt thereof.

38. A compound according to claim 1, wherein said compound is (2S)-2-{[4-(6-Bromoquinolin-2-yl)piperazin-1-yl]methyl}-8-methyl-2,3-dihydro[1,4]dioxino[2,3-f]quinoline or a pharmaceutically acceptable salt thereof.

39. A compound according to claim 1, wherein said compound is (2S)-2-{[4-(6-methoxyquinolin-2-yl)piperazin-1-yl]methyl]-8-methyl-2,3-dihydro[1,4]dioxino[2,3-f]quinoline or a pharmaceutically acceptable salt thereof.

40. A compound according to claim 1, wherein said compound is (2S)-2-{[4-(6-Trifluoromethoxyquinolin-2-yl)piperazin-1-yl]methyl]-8-methyl-2,3-dihydro[1,4]dioxino[2,3-f]quinoline or a pharmaceutically acceptable salt thereof.

41. A compound according to claim 1, wherein said compound is 2-[4-(6-Fluoro-quinolin-2-yl)-piperazin-1-yl-methyl]-8-methyl-2,3-dihydro-[1,4]dioxino[2,3-f]quinoline or a pharmaceutically acceptable salt thereof.

42. A compound according to claim 1, wherein said compound is (2S)-2-{[4-(6-methoxyquinolin-2-yl)-1,4-diazepan-1-yl]methyl]-8-methyl-2,3-dihydro[1,4]dioxino[2,3-f]quinoline or a pharmaceutically acceptable salt thereof.

43. A compound according to claim 1, wherein said compound is2-(4-{[(2S)-8-Methyl-2,3-dihydro[1,4]dioxino[2,3-f]quinolin-2-yl]methyl}1,4-diazepan-1-yl)quinoline-6-carbonitrile or a pharmaceutically acceptable salt thereof.

44. A compound according to claim 1, wherein said compound is (2S)-2-{[4-(6-Trifluoromethoxy-quinolin-2-yl)-1,4-diazepan-1-yl]methyl]-8-methyl-2,3-dihydro[1,4]dioxino[2,3-f]quinoline or a pharmaceutically acceptable salt thereof.

45. A compound according to claim 1, wherein said compound is 2-[4-(6-Fluoro-quinolin-2-yl)-[1,4]diazepan-1-ylmethyl]-8-methyl-2,3-dihydro-[1,4]dioxino[2,3-f]quinoline or a pharmaceutically acceptable salt thereof.

46. A compound according to claim 1, wherein said compound is (2S)-2-{[4-(6-Bromo-quinolin-2-yl)-1,4-diazepan-1-yl]methyl]-8-methyl-2,3-dihydro[1,4]dioxino[2,3-f]quinoline or a pharmaceutically acceptable salt thereof.

47. A compound according to claim 1, wherein said compound is 8-Methyl-2-(4-quinolin-2-yl-[1,4]diazepan-1-ylmethyl)-2,3-dihydro-[1,4]dioxino[2,3-f]quinoline or a pharmaceutically acceptable salt thereof.

48. A compound according to claim 1, wherein said compound is 8-Methyl-2-[4-(4-methyl-quinolin-2-yl)-[1,4]diazepan-1-ylmethyl]-2,3-dihydro[1,4]dioxino[2,3-f]quinoline or a pharmaceutically acceptable salt thereof.

49. A method of treating a subject suffering from a condition selected from depression, anxiety, panic disorder, post-traumatic stress disorder, premenstrual dysphoric disorder, attention deficit disorder, obsessive-compulsive disorder, social anxiety disorder, generalized anxiety disorder, obesity, eating disorders, vasomotor flushing, alcohol addiction, and sexual dysfunction, comprising the step of:
providing to said subject suffering from said condition, a therapeutically effective amount of a compound according to claim 1 or a pharmaceutically acceptable salt thereof.

50. A method according to claim 49, wherein the condition is depression.

51. A method according to claim 49, wherein the condition is selected from the group consisting of obsessive-compulsive disorder, panic attacks, generalized anxiety disorder, and social anxiety disorder.

52. A pharmaceutical composition, comprising:
an effective amount of a compound according to claim 1 or a pharmaceutically acceptable salt thereof; and
a pharmaceutically acceptable carrier or excipient.

* * * * *